(12) United States Patent
Freeman et al.

(10) Patent No.: US 11,596,638 B2
(45) Date of Patent: Mar. 7, 2023

(54) 18-MC FOR TREATMENT OF SUBSTANCE USE DISORDERS

(71) Applicant: Mind Medicine, Inc., Reno, NV (US)

(72) Inventors: Scott Freeman, Las Vegas, NV (US); Stots B. Reele, Scottsville, VA (US); Jeanne Bonelle, Castro Valley, CA (US)

(73) Assignee: Mind Medicine, Inc, New York, NY (US)

( * ) Notice: Subject to any disclaimer, the term of this patent is extended or adjusted under 35 U.S.C. 154(b) by 99 days.

(21) Appl. No.: 17/060,443

(22) Filed: Oct. 1, 2020

(65) Prior Publication Data

US 2021/0093643 A1   Apr. 1, 2021

Related U.S. Application Data

(60) Provisional application No. 62/908,754, filed on Oct. 1, 2019.

(51) Int. Cl.
| | | |
|---|---|---|
| *A61K 31/55* | (2006.01) | |
| *A61P 25/30* | (2006.01) | |
| *A61K 9/00* | (2006.01) | |

(52) U.S. Cl.
CPC ............ *A61K 31/55* (2013.01); *A61K 9/0053* (2013.01); *A61P 25/30* (2018.01)

(58) Field of Classification Search
CPC ..................................................... A61K 31/55
See application file for complete search history.

(56) References Cited

U.S. PATENT DOCUMENTS

| | | | |
|---|---|---|---|
| 9,289,425 B2 * | 3/2016 | Wyse ..................... | A61K 47/12 |
| 2002/0103109 A1 | 8/2002 | Glick | |
| 2015/0051192 A1 | 2/2015 | Glick et al. | |
| 2015/0246055 A1 * | 9/2015 | Friedhoff ............... | A61K 31/55 |
| | | | 514/214.02 |
| 2015/0258108 A1 | 9/2015 | Maillet et al. | |
| 2015/0258109 A1 | 9/2015 | Maillet et al. | |

OTHER PUBLICATIONS

Glick et al. NeuroReport, 2000, 11(9): 2013-2015.*
McCallum et al., Neuroscience Letters, 2009, 458(2): 57-59.*
Zhang et al. 'Metabolism of 18-Methoxycoronaridine, an Ibogaine Analog, to 18-Hydroxycoronaridine by Genetically Variable CYP2C19'. Drug Metabolism and Disposition, Jun. 1, 2002 (Jun. 1, 2002). vol. 30, pp. 663-669; p. 664.
Glick et al. '18-Mthoxycoronaridine (18-MC) and ibogaine: comparison of antiaddictive efficacy, toxicity, and mechanisms of action'. Annals of the New York Academy of Sciences, Sep. 2000, vol. 914, pp. 369-386 Abstract.

* cited by examiner

*Primary Examiner* — Rei Tsang Shiao
(74) *Attorney, Agent, or Firm* — Kohn & Associates, PLLC

(57) ABSTRACT

A composition for treating substance use disorders of an effective amount of 18-Methoxycoronaridine salt (18-MC) in a pharmaceutical carrier. A method of treating substance use disorders, by administering an effective amount of 18-Methoxycoronaridine salt (18-MC) in a pharmaceutical carrier to an individual and preventing substance abuse in the individual. A method of preventing addictive behavior in an individual. A method of preventing craving in an individual. A composition of a metabolite of 18-MC salt. A method of treating substance use disorders by administering an effective amount of a metabolite of 18-MC salt in a pharmaceutical carrier to an individual and preventing substance abuse in the individual. A composition having various pharmacokinetic profiles as shown in the Figures.

8 Claims, 15 Drawing Sheets

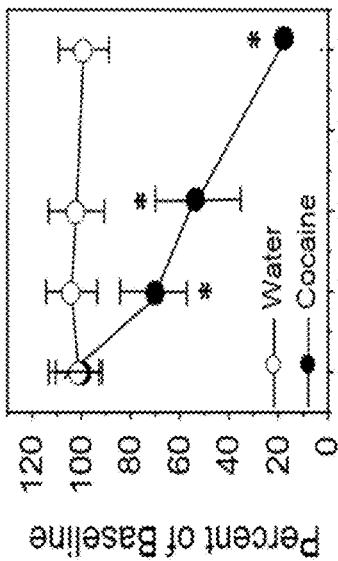
FIGURE 1
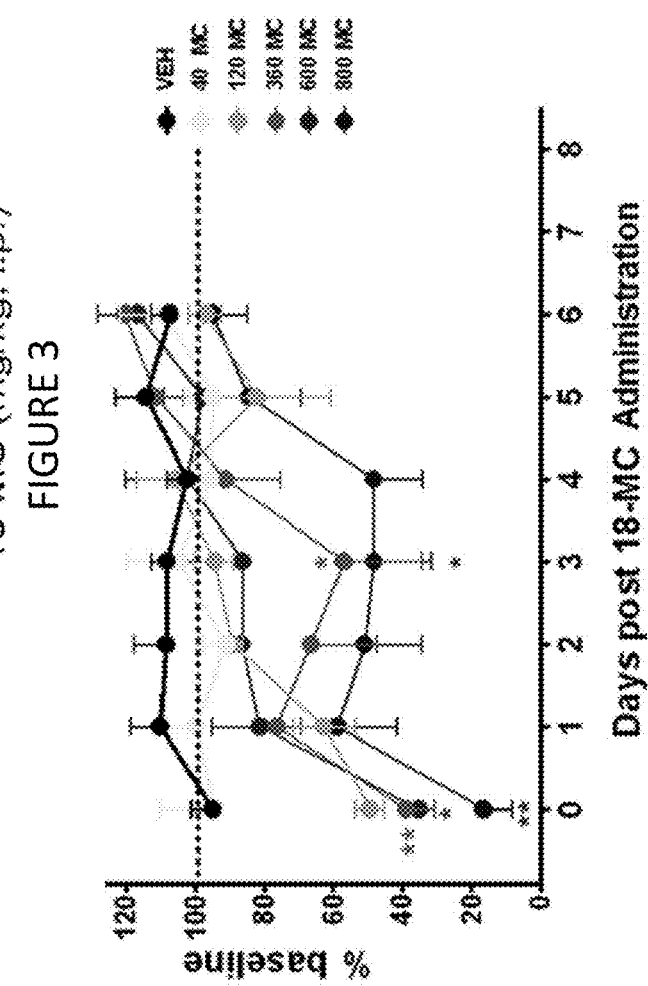
FIGURE 3
FIGURE 4
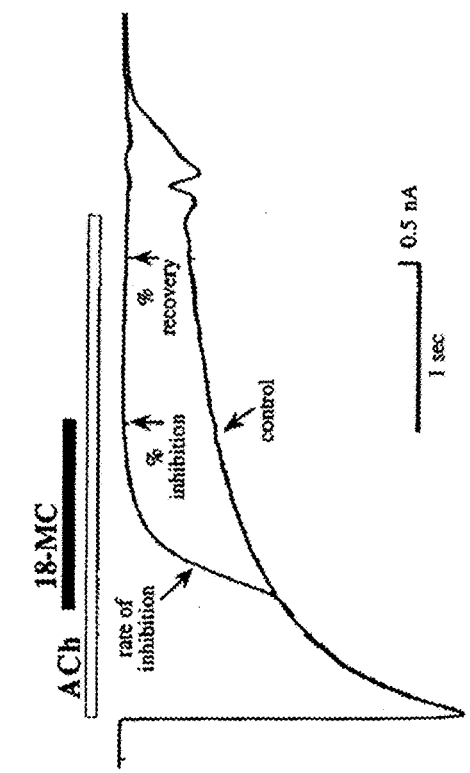
FIGURE 2

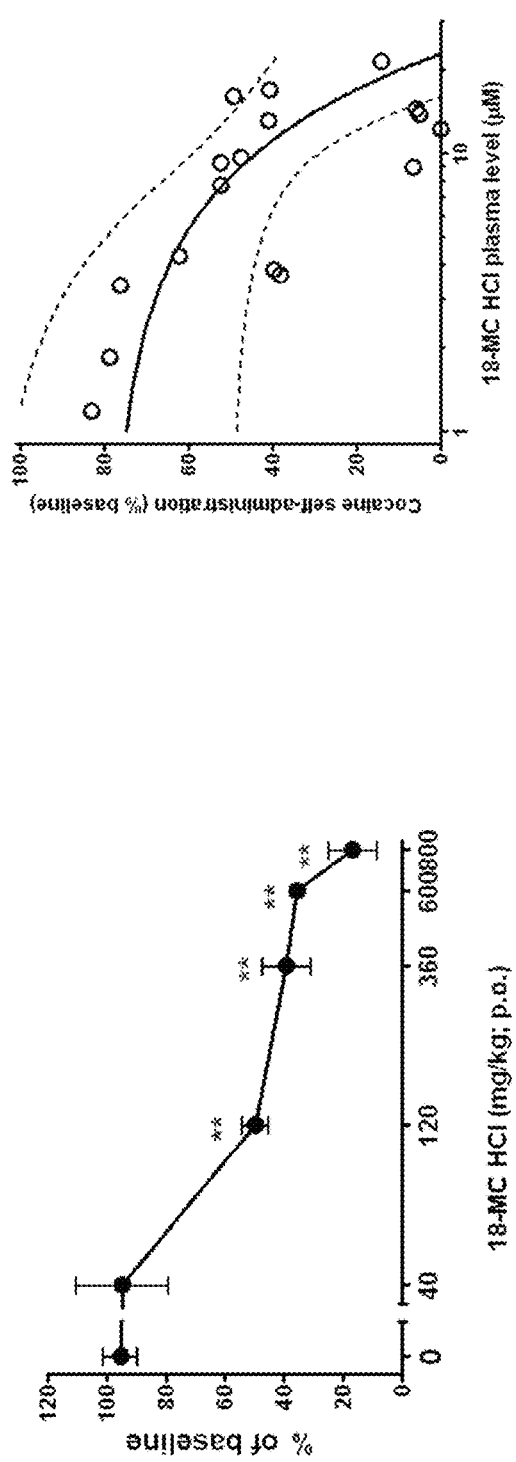
FIGURE 5
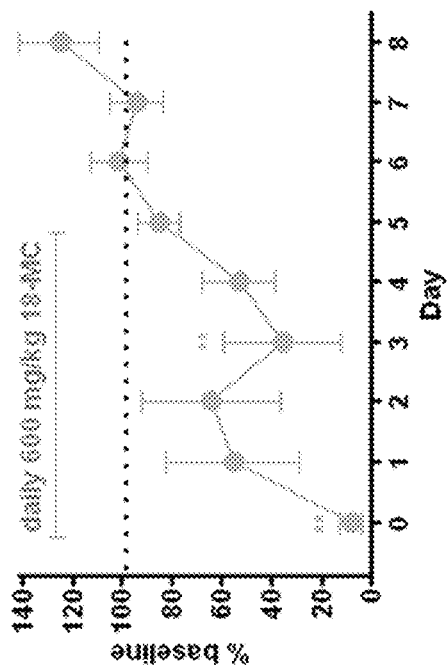
FIGURE 7
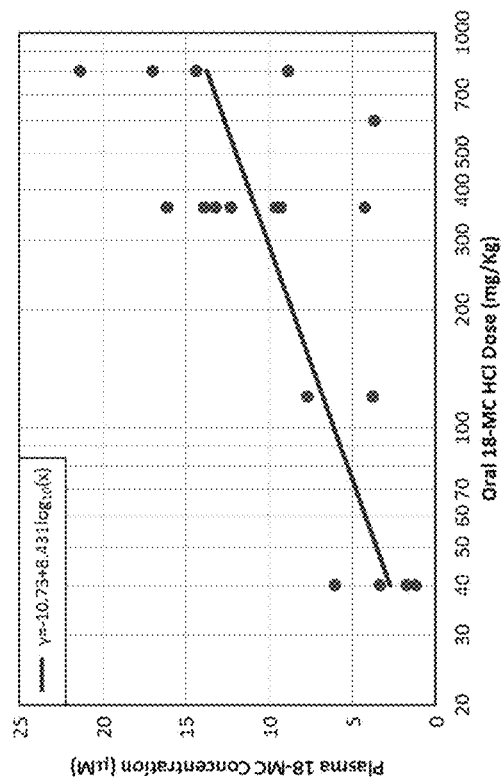
FIGURE 8
FIGURE 6

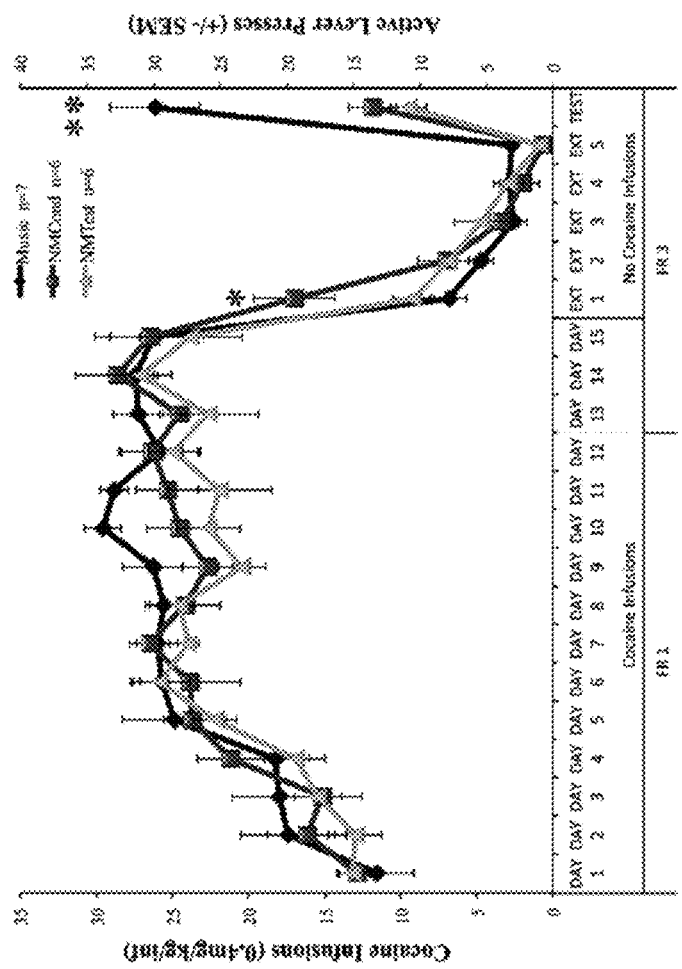
FIGURE 11
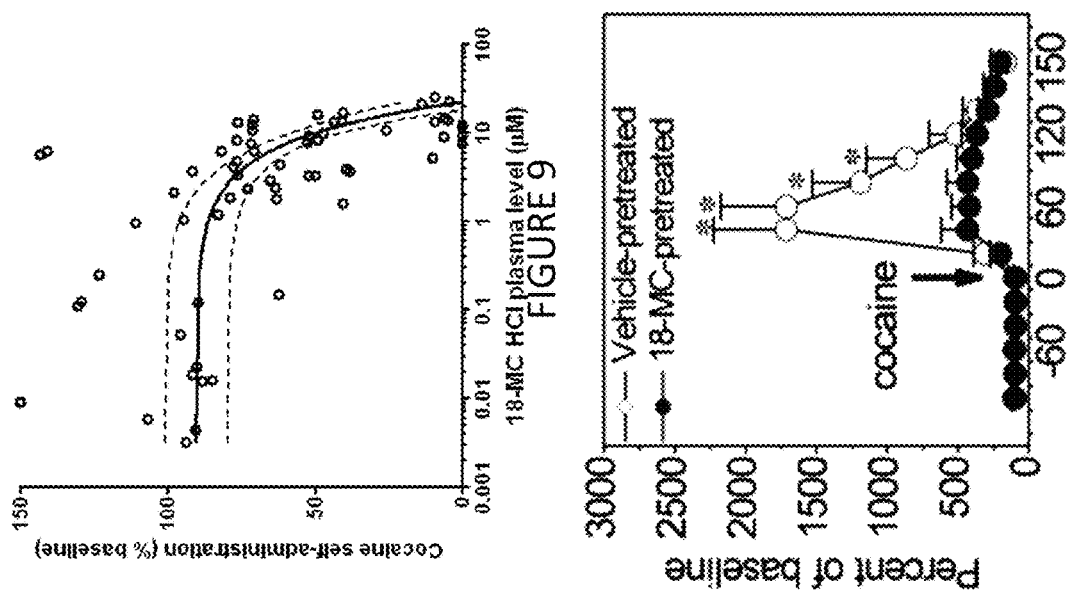
FIGURE 9
FIGURE 10

Synthetic M5

18-MC FOR TREATMENT OF SUBSTANCE USE DISORDERS

BACKGROUND OF THE INVENTION

1. Technical Field

The present invention relates to compositions and methods for treating substance use disorders.

2. Background Art

Substance use disorders (SUD) represent a major public health and social issue worldwide. In the United States (US), drug and alcohol misuse and abuse are currently leading causes of death, disability, and disease. In addition, current misuse and abuse of prescription medications (including opioids and benzodiazepines) is epidemic, doubling in the last decade and now responsible for more deaths than motor vehicle accidents (Centers for Disease Control and Prevention [CDC], 2011). The financial cost of SUDs to society, including the cost of treating drug and alcohol abuse, the cost of secondary illnesses and injuries, and lost earnings and years of life due to abusers' illness, incarcerations, and premature death, is staggering. It has been estimated that the cost of drug and alcohol abuse to US society is nearly a half trillion dollars each year (National Institute on Drug Abuse [NIDA], 2010).

Currently, there are limited effective pharmacotherapies for the treatment of SUDs. The only medications approved for SUDs by the US Food and Drug Administration (FDA) are for nicotine and opiate use disorders, and their efficacy is considered to be modest (Marsch, 1998).

U.S. patent application Ser. No. 14/387,339 to Glick, et al. discloses methods of preventing drug relapse, especially during cue inducement, by administering an effective amount of an α3β4 nicotinic antagonist (18-Methoxycoronaridine) to a mammal, after an initial period of drug use, and preventing a relapse of drug use. It was shown that rats conditioned with a musical cue show increased drug-seeking behaviors with cocaine when compared to control groups. At the time of this application, the mechanism of action of 18-MC was not completely understood, nor was there evidence that it would be effective in humans.

Therefore, a need exists for safe, effective, orally-available, and low-cost pharmacologic approaches to treat SUDs, particularly cocaine disorders for which there are currently no approved therapies.

SUMMARY OF THE INVENTION

The present invention provides for a composition for treating substance use disorders of an effective amount of 18-Methoxycoronaridine salt (18-MC) in a pharmaceutical carrier.

The present invention provides for a method of treating substance use disorders, by administering an effective amount of 18-Methoxycoronaridine salt (18-MC) in a pharmaceutical carrier to an individual and preventing substance abuse in the individual.

The present invention provides for a method of preventing addictive behavior in an individual, by administering an effective amount of 18-Methoxycoronaridine salt (18-MC) in a pharmaceutical carrier to an individual and preventing addictive behavior in the individual.

The present invention also provides for a method of preventing craving in an individual, by administering an effective amount of 18-Methoxycoronaridine salt (18-MC) in a pharmaceutical carrier to an individual and preventing craving in the individual.

The present invention also provides for the composition of a metabolite of 18-MC salt.

The present invention further provides for a method of treating substance use disorders by administering an effective amount of a metabolite of 18-MC salt in a pharmaceutical carrier to an individual and preventing substance abuse in the individual.

DESCRIPTION OF THE DRAWINGS

Other advantages of the present invention are readily appreciated as the same becomes better understood by reference to the following detailed description when considered in connection with the accompanying drawings wherein:

FIG. 1 is the chemical structure of 18-Methoxycoronaridine hydrochloride (18-MC HCl);

FIG. 2 is a representative tracing for 18-MC receptor binding;

FIG. 3 is a graph of 18-MC effect on cocaine self-administration in rats;

FIG. 4 is a graph of acute effects of 18-MC on cocaine self-administration in rats;

FIG. 5 is a dose-response curve for 18-MC effect on cocaine self-administration in rats, measured 1 hour after treatment;

FIG. 6 is a graph of plasma concentrations of 18-MC following single oral administration in rats;

FIG. 7 is a graph of the relationship between inhibition of cocaine self-administration and plasma concentrations;

FIG. 8 is a graph of the inhibition of cocaine self-administration following repeat dosing with 600 mg/kg/day 18-MC for 5 days in rats;

FIG. 9 is a graph of the relationship between inhibition of cocaine self-administration and 18-MC plasma concentrations in rats following a single dose administration;

FIG. 10 is a graph of 18-MC effect on sensitized dopamine response in rats;

FIG. 11 is a graph showing effects of music conditioning on active lever responding during daily cocaine self-administration sessions, extinction, and the reinstatement test session in rats;

DETAILED DESCRIPTION OF THE INVENTION

Figure 13:
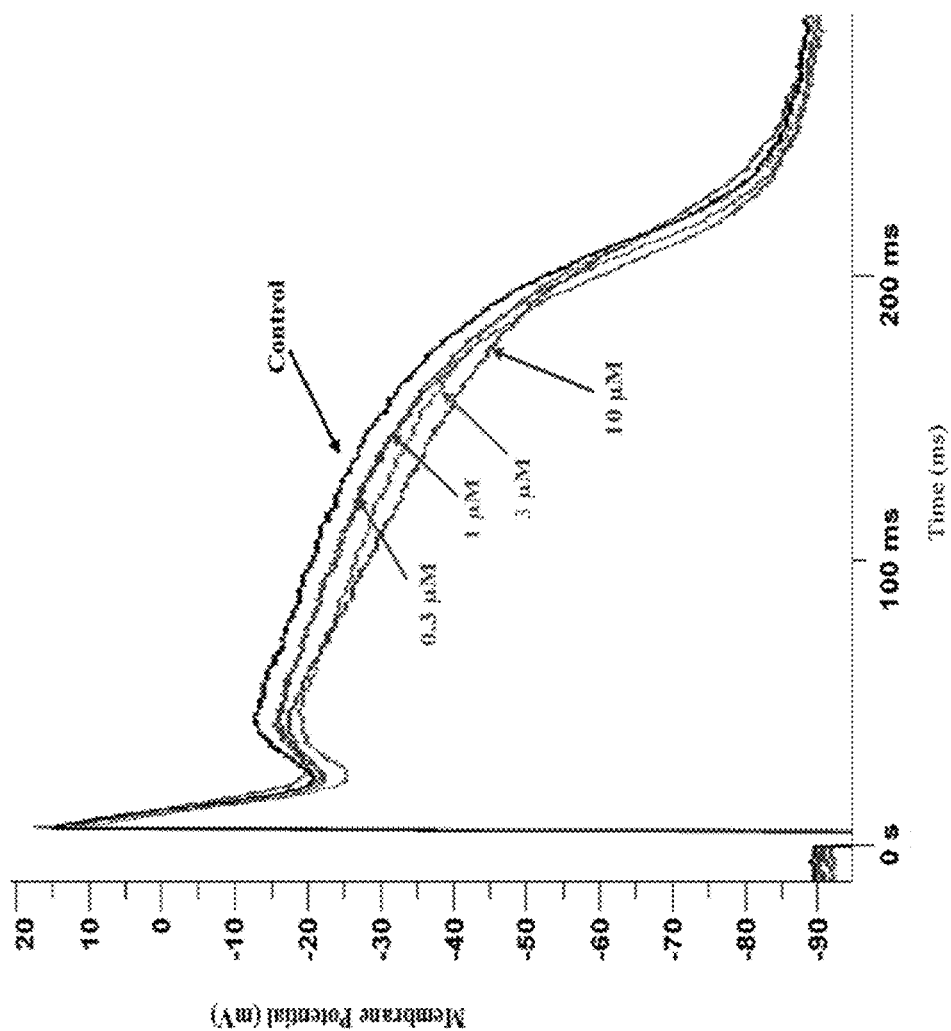
FIG. 13 is a graph of the effect of 18-MC on action potential duration in rabbit cardiac Purkinje fibers.

The present invention provides for a composition and method for treating substance use disorders. More specifically, the present invention provides for a composition for treating substance use disorders of an effective amount of 18-Methoxycoronaridine salt (18-MC) in a pharmaceutical carrier.

"Substance use disorder" as used herein, refers to cocaine abuse, smoking cessation, opiate withdrawal, or any other substance that can be abused. In other words, an individual can be treated for using substances such as cocaine, nicotine, opiates, alcohol, morphine, methamphetamine, or other substances. Behavioral disorders can also be treated in the present invention.

"Individual" as used herein, refers to mammals, and preferably to humans. While 18-MC has previously been used in rats to prevent cue-induced drug relapse, it was unexpected that it would work in humans. Furthermore, the data shown below regarding human studies was not predictable based on animal studies.

18-MC has demonstrated activity in several animal models of addiction, including those involving nicotine, cocaine, alcohol, morphine, and methamphetamine. 18-MC is effective against many addictive substances because it works in the brain's pleasure center to prevent craving.

The free base 18-methoxycoronaridine (18-MC) is a synthetic coronaridine congener and a specific negative allosteric modulator (antagonist) of α3β4 nicotinic cholinergic receptors; it indirectly modulates the dopaminergic mesolimbic pathway via blockade of α3β4 nicotinic receptors in the habenulo-interpeduncular pathway and the basolateral amygdala (Glick et al., 2008). Animal studies have demonstrated that 18-MC significantly reduces drug self-administration in a number of substance use models (nicotine, alcohol, morphine, cocaine and methamphetamine) at dosages as low as 10 mg/kg i.p. (Glick et al., 1994; Rezvani et al., 1995; Glick et al., 1996; Glick et al., 1998; Glick et al., 2000a). More recently, 18-MC has been shown in an animal model to attenuate effects of the environmental cues responsible for stimulating cocaine-seeking or "craving" behaviors (Polston et al., 2012, and U.S. patent application Ser. No. 14/387,339 to Glick, et al.). This property of 18-MC could potentially help address the craving component of human addictive behaviors.

The salt is preferably hydrochloride, however other salts can also be used. 18-MC HCl is a soluble salt form of 18-MC, shown in FIG. 1 ($C_{22}H_{29}N_2O_3Cl$, molecular weight 404.97 g/mol). 18-MC HCl is the lead candidate from a library of synthetic coronaridine congeners described by Glick and colleagues (1994). It has a broader potential application in SUDs because its mechanism of action is central to addiction behavior per se, rather than to specific chemical substances of abuse. 18-MC HCl is a specific negative allosteric modulator or (antagonist) of α3β4 nicotinic cholinergic receptors that indirectly modulates the dopaminergic mesolimbic pathway by blocking α3β4 nicotinic receptors in the habenulo-interpeduncular pathway and the basolateral amygdala (Glick et al, 2008). Animal studies have demonstrated that a single dose of 18-MC HCl as low as 10 mg/kg i.p. can significantly reduce drug self-administration in a number of substance use models (nicotine, alcohol, morphine, cocaine and methamphetamine) (Glick et al, 1994; Rezvani et al, 1995; Glick et al, 1996; Glick et al, 1998; Glick et al, 2000a). More recently, 18-MC HCl has been shown in an animal model to attenuate the effects of environmental cues responsible for stimulating cocaine-seeking or "craving" behaviors (Polston et al, 2012). This property of 18-MC could potentially help address another important component of human addictive behaviors—namely, craving.

18-MC reduces the reinforcing effects of addictive drugs and decreases self-administration of cocaine and other addictive drugs in rats. Mechanistic studies have shown that 18-MC acts as an allosteric, noncompetitive antagonist of the nicotinic acetylcholine (nACh) α3β4 receptor. The α3β4 nACh receptor is predominantly localized in two brain nuclei: the medial habenula and the interpeduncular nucleus. 18-MC has at least 20-fold higher affinity for α3β4 than for α4β2 nACh receptors (which are expressed ubiquitously in the brain), or for NMDA or 5HT3 receptors (Glick et al, 2002). Local administration of 18-MC into the interpeduncular nuclei or medial habenula can reduce drug self-administration (e.g., of methamphetamine), whereas local administration of 18-MC into the ventral tegmental area has no such effect. Consistent with these behavioral findings, systemic administration of 18-MC attenuates the sensitizing effects of repeated cocaine treatments on dopamine release in the nucleus accumbens. Lastly, in a well-characterized animal model for "craving" behaviors, 18-MC attenuated the effects of the environmental cues responsible for stimulating cocaine-seeking behavior.

Formulation and Dosing

18-MC HCl can be supplied as a dry powder packaged in double plastic bags in an HDPE bottle with desiccant. The 18-MC HCl can be formulated at the clinical site into a solution for dosing patients. 18-MC HCl is soluble in water (pH 2.5) up to 30 g/ml. 18-MC HCl is poorly soluble in aqueous solution at neutral and alkaline pH. 18-MC HCl is freely soluble in dimethyl sulfoxide (DMSO). Based on the properties of the compound, it can also be formulated in a solid oral formulation (tablet, capsule, sachets, granules, etc.)

Most preferably, an oral dose of the composition is used. An oral dosing formulation was validated by a GLP study. The maximum solubility of 18-MC HCl is 40 mg/mL in 5% dextrose (pH 3.0). 18-MC HCl properties (homogeneity and concentration acceptability, solubility, and stability after 10 days of refrigerated storage) met the applicable ICH criteria. The 18-MC HCl dosing solution also met the required stability criteria after 3 freeze-thaw (20° C.) cycles.

18-MC HCl is synthesized in five steps, starting with two proprietary, non-GMP starting materials (an aldehyde and an indole) and completed as the HCl salt of 18-MC. The 18-MC HCl is a racemate with a 1:1 ratio of the two enantiomers.

18-MC can be administered in a dose from 0.01-10 mg/kg. Animal studies described below showed that the no-observed-effect level (NOEL) and no-observed-adverseeffect level (NOAEL) were 90 mg/kg and 400 mg/kg. Clinical studies in Example 6 showed that a 20 mg dose once a day is safe in humans. A more preferable dose can be 4 mg twice a day in humans.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Pharmacokinetics

In all the species tested in pre-clinical studies, 18-MC is rapidly absorbed following oral administration with $T_{max}$ occurring in less than 0.5 hours following oral administration. After oral administration, the elimination of 18-MC is multi-compartmental. In plasma, 18-MC is highly protein bound (92% to 98%). 18-MC is also rapidly and extensively metabolized, presumably by first pass metabolism. At least 13 different metabolites have been detected both in vitro and in vivo, further described below (M1-M9, P1-P3). The major metabolites (those with exposure greater than 10% of the total drug related material) appear to change with the dose and duration of dosing. Major metabolites include M2, M4, M5, M8, M9 and P2 depending on the animal species tested, and the dose and duration of dosing.

When administered orally, 18-MC is a very minor percentage of the circulating drug material (<1% in the mouse after a dose of 25 mg/kg/day and <3% in the monkey after a dose of 300 mg/kg/day).

In a GLP oral toxicology study in mice, after 14 days of administration of 25 mg/kg 18-MC HCl, the major metabolites were M2>M4»M9>M8, with 18-MC being <1% of all drug-related material. The exposure to 18-MC were $C_{max}$ 105 ng/mL and AUC 251 ng×hr/mL. The elimination half-life following an oral dose of 25 mg/kg 18-MC HCl was 3 to 4 hours in both sexes and about 2 hours for the major metabolites.

In a GLP oral toxicology study in monkeys, after 14 days of administration of 300 mg/kg 18-MC HCl, the relative frequency of metabolites was M5>>M2>P2, with 18-MC less than 3% of the total circulating drug-related material. On Day 14, the exposure to 18-MC was $C_{max}$ 144 ng/mL and AUC 1210 ng×hr/mL.

The enzymes that metabolize 18-MC have not yet been identified, but 18-MC has been shown to moderately inhibit CYP2C9 and CYP2C19 and, to a lesser extent, CYP2C8, CYP2E1 and CYP3A4.

Pharmacology

The pharmacological activity of 18-MC and two of the major metabolites were tested by whole-cell patch clamp recording of HEK 293 cells expressing recombinant α3β4 nACh receptors (Pace et al (2004)). Application of 1 mM acetylcholine (Ach) produced a large, inward, desensitizing current similar. 18-MC inhibited the Ach-evoked currents with an $IC_{50}$ value of 0.8 µM.

The binding potential of 18-MC with 64 neurotransmitter-related binding sites was evaluated. At 10 μM 18-MC, binding was seen to the adrenergic alpha-1 receptor, Mu opioid receptor, and sodium site 2 channel ligands; this concentration of 18-MC, however, is several orders of magnitude greater than the expected human plasma concentration of unbound 18-MC.

In a CNS safety pharmacology study, as would be expected given the known pharmacological activity of 18-MC and its effects upon central dopaminergic activity, the administration of 18-MC in rats was characterized by depressed motor function and increased sedation. Other effects included slower respiration rate, decreased cutaneous blood flow, increased pupil diameter and decreased body temperature. All of these findings were transient and dose dependent with increased frequency and occurrence corresponding to increased dose. The time of peak effect occurred between 90 and 150 minutes post-dosing and subsided at 6 hours post-dose.

In vitro, 18-MC inhibited hERG ionic conductance and reduced action potential duration in rabbit purkinje fibers. However, single oral administration of 18-MC HCl at doses of 30, 90, or 270 mg/kg to male radio telemetry-implanted cynomolgus monkeys did not affect cardiovascular parameters, body temperature, or respiratory parameters. Apart from emesis at the highest dose, 18-MC HCl was generally well tolerated in monkeys. The no-observed-effect level (NOEL) on both the cardiovascular and the respiratory systems was determined to be 270 mg/kg. There was also no evidence of any electrocardiographic abnormalities in monkeys treated with 18-MC HCl for 2 weeks up to an oral dose of 300 mg/kg/day in the 2-week toxicology study. The basis for a potential discrepancy between the in vitro and in vivo findings is not known but could be related to differences in the disposition of 18-MC such as metabolism and protein binding, since 18-MC is both highly metabolized and highly protein bound in vivo. In both mice and monkeys, for instance, 18-MC is significantly metabolized with parent drug representing only a fraction of the exposure represented by metabolites.

18-MC has been studied for its effects on the hERG channel and the rabbit Purkinje fibers action potential duration (ADP). 18-MC prolonged the hERG and decreased the ADP. The significance of these observations is not known because 18-MC is only a minor component of the circulating 18-MC drug related material, and information on the metabolites have not been studied in these in vitro systems. In instrumented monkeys, the administration of 18-MC had no effect on electrocardiographic intervals or cardiovascular function. The collective in vitro and in vivo data suggest that 18-MC does not pose a significant pro-arrhythmic liability. Given the low proposed starting dose and cautious dose escalation scheme, the risk for untoward cardiovascular events in a clinical trial is considered low.

During the dose finding studies in animals, acute death was observed at some doses within 1.5 to 4 hours after 18-MC HCl administration, with mice being the most sensitive. However, the cause of death could not be identified upon necropsy. The acute effects of oral administration in mice of 100 mg/kg followed 8 hours later by a second dose of 200 mg/kg of 18-MC HCl on arterial blood pressure, heart rate, and body temperature were further investigated in radio-telemetered mice. After the initial dose, behavioral effects prior to death included tremors, twitches, abnormal gait, lethargy, decreased motor activity, increased response to touch and startle, seizures, gasping and slow respirations, exophthalmia and stupor. The peak effects occurred between 90 and 150 minutes after the oral administration of 18-MC HCl. Following the second dose, all animals exhibited similar reactions to the upper dose of 200 mg/kg and were within one hour of dosing as follows: average heart rate decreased about 50%, and significant decreases in systolic and diastolic blood pressure, and internal body temperature were seen. Terminally, there was a further decrease in all of the parameters being measured, with the temperature falling steeply (to as low as 22° C. in one mouse) before the mice died.

Based on the safety pharmacology, clinical pathological and vital signs (including heart rate, blood pressure, and body temperature) can be closely monitored as changes in neurobehavior, clinical pathology, vital signs or body temperature are expected to serve as useful premonitory markers by which to limit dosing and protect subjects against the occurrence of significant adverse effects.

Toxicology

The results of single-dose studies in rodents, dogs, and monkeys indicated as expected, the known pharmacological profile of 18-MC, that the oral administration of 18-MC HCl produced transient, dose-related neurobehavioral changes. Single doses up to 300-400 mg/kg and 800 mg/kg appeared to be generally well tolerated in monkeys and rats, respectively (one monkey treated with 400 mg/kg died in the 2-week GLP study on Day 1 of dosing). Emesis in dogs was seen at a lower dose (100 mg/kg), limiting the utility of this model for characterizing the toxicology profile of 18-MC HCl. In mice, mortality was consistently seen following single doses 150 mg/kg. Preliminary 5-day repeat-dose range-finding studies were conducted in mice, rats and monkeys. The definitive 14-day studies in mouse and monkey yielded generally similar results to those observed in the 5-day studies.

In a 2-week GLP study in mice (the most sensitive species), doses of 0 (vehicle), 25, 50, or 100 mg/kg/day were administered for 14 days by oral gavage following a 2 to 4 day dose-up titration. In the GLP study, two male mice in the 100 mg/kg/day group were found dead on Days −1 and 12. The cause of death in the two animals was undetermined though anatomical pathology findings consisted of atrial and/or ventricular dilatation. In the animal that died on Day −1, this animal had received 3 doses of 18-MC HCl (25, 50 and 75 mg/kg) as part of an up-titration to the top dose of 100 mg/kg. There were no clinical findings which preceded the death of this animal. The other animal that died on Day 12 also exhibited similar anatomical pathology changes in the heart as well as several neurobehavioral observations (including clonic convulsions) prior to death clearly indicating that the death was test article-related. Clinical pathology effects in surviving animals were limited to dose-related reductions in total white blood cell counts and lymphocytes and a slight increase in serum cholesterol (100 mg/kg/day males). The no-observed-adverse-effect-level (NOAEL) in this study was 50 mg/kg/day in males (based upon the death of two high-dose males) and 100 mg/kg/day in females. There were no histopathology findings (including no neuropathology findings) in the dead mice that were attributable to 18-MC HCl.

In a 2-week GLP study in monkeys, neurobehavioral signs consistent with the expected pharmacological activity of 18-MC HCl were noted in high-dose animals (5 males/5 females) and one male died following the administration of 400 mg/kg on the first day of dosing (the dose level was reduced from 400 mg/kg to 300 mg/kg from Day 2 onward). There were no other deaths in this study. Treatment with 18-MC HCl was associated with a slight reduction in body weight/body weight gain (doses 50 mg/kg/day), hematological effects, and bone marrow changes in 150 mg/kg/day males and 400/300 mg/kg/day animals. The predominant serum chemistry change noted was a reduction in alkaline phosphatase relative to controls across all dose levels; this decrease was not judged to be of toxicologic importance. Mildly reduced weight in the thymus was observed at 50 mg/kg/day and at 400/300 mg/kg/day, which correlated microscopically with test article-related generalized lymphoid depletion. No neuropathological alterations attributable to 18-MC HCl were observed. Based upon the results of this study, the NOAEL in this study was 50 mg/kg/day.

In the genetic toxicology studies, although 18-MC HCl was found to be positive in the in vitro chromosome aberration assay in the presence (but not absence) of metabolic activation, no evidence of genotoxicity was seen in the in vitro Ames assay or in the two in vivo studies conducted (mouse micronucleus and comet assays). The collective results indicate that 18-MC does not pose a significant genotoxic risk.

Clinical Study

An FTIH study of 18-MC HCl described in Example 6 is a Phase 1, randomized, double-blind, placebo-controlled, single ascending dose study to evaluate the safety, tolerability, and pharmacokinetics (PK) of 18-MC.

The primary objective of the study is to assess the safety and tolerability of 18-MC HCl following oral administration of single ascending doses given to healthy male and female (of non-childbearing potential) volunteers.

The secondary objectives are 1) to characterize the PK of 18-MC in plasma following oral administration of single ascending doses, 2) to detect and quantify metabolites (if a validated assay is available or report the relative metabolite ratios) of 18-MC in plasma, 3) to characterize the PD effects and duration of PD effects of 18-MC following oral administration of single ascending doses, 4) as an experimental objective, the relative concentration of 18-MC and metabolites in the urine may be determined.

Based upon the nonclinical toxicology studies conducted to date, the predominant adverse findings in mice and monkeys were exaggerated acute neurobehavioral findings consistent with the known pharmacological activity of 18-MC. In the pivotal 2-week studies, 18-MC HCl was well tolerated in mice at doses up to 100 mg/kg/day in female mice and 50 mg/kg/day in male mice, which correspond to HEDs of 8 and 4 mg/kg/day, respectively. These doses also correspond to the highest non-lethal doses in this species. In monkeys, 18-MC HCl was well tolerated at a dose of 50 mg/kg/day (corresponding to an HED of 16 mg/kg/day). The highest non-lethal dose for monkeys was 300 mg/kg.

In the FTIH study, the initial clinical dose was proposed to be 20 mg which is based on the non-lethal dose in the most sensitive species, mouse, and which was determined as follows. The non-lethal dose in mice is 50 mg/kg which has a HED of 4 mg/kg. This value is multiplied by 1/10 for an additional safety correction factor resulting in an HED of 0.4 mg/kg (which corresponds to a human dose of 28 mg). To be conservative then, the starting dose can be 20 mg instead of 28 mg for an additional safety factor. The study showed that high plasma levels occurred at 20 mg, and so a lower dose of 4 mg twice daily was examined. No serious adverse events were reported.

For dose escalation in the FTIH study, drug exposure limits can be set by 1/10 of the exposure in the mouse, and safety stopping criteria are detailed in the protocol.

The studies showed that the pharmacokinetics appeared to follow a multiple-compartment model and the elimination half-life of 18-MC and the metabolites was about 48 hours. 18-MC has a short distribution half-life and longer terminal half-life.

The results from the nonclinical safety pharmacology and toxicology studies predict that 18-MC can affect the central and/or autonomic nervous, cardiovascular, immune and hematopoietic systems at doses significantly higher than are proposed. The protocol incorporates appropriate precautionary measures and a cautious dose-escalation scheme to limit the chance for significant adverse events. Based upon the results of safety pharmacology and mouse toxicology studies, vital signs (including body temperature) can be closely monitored as part of the proposed clinical trial.

The present invention provides for a method of treating substance use disorders, by administering an effective amount of 18-MC HCl in a pharmaceutical carrier to an individual and preventing substance abuse. Preferably, the 18-MC HCl is in an oral dosage form. The substance can be any of those described above. Administration can be at any of the dosing ranges described above, and more preferably 20 mg or less per day. 18-MC HCl is highly protein bound and undergoes multi-compartmental elimination. The method further includes the step of 18-MC HCl blocking $\alpha 3 \beta 4$ nicotinic receptors in the habenulo-interpeduncular pathway and the basolateral amygdala. The 18-MC HCl can further inhibit enzymes CYP2C9, CYP2C19, CYP2C8, CYP2E1, and CYP3A4 as described below in Example 4. Example 1 shows that 18-MC HCl can decrease cocaine self-administration dose dependently and has greater effects at higher plasma concentrations. 18-MC HCl can reverse the sensitized dopaminergic response to drugs and decrease the rewarding effect of drugs.

The present invention provides for a method of preventing addictive behavior in an individual, by administering an effective amount of 18-MC HCl in a pharmaceutical carrier to an individual and preventing addictive behavior in the individual. Preferably, the 18-MC HCl is in an oral dosage form. The substance can be any of those described above. Administration can be at any of the dosing ranges described above, and more preferably 20 mg or less per day. The method further includes the step of 18-MC blocking $\alpha 3 \beta 4$ nicotinic receptors in the habenulo-interpeduncular pathway and the basolateral amygdala. The 18-MC can further inhibit enzymes CYP2C9, CYP2C19, CYP2C8, CYP2E1, and CYP3A4.

The present invention also provides for a method of preventing craving in an individual, by administering an effective amount of 18-MC HCl in a pharmaceutical carrier to an individual and preventing craving in the individual. Preferably, the 18-MC HCl is in an oral dosage form. The substance can be any of those described above. Administration can be at any of the dosing ranges described above, and more preferably 20 mg or less per day. 18-MC is highly protein bound and undergoes multi-compartmental elimination. The method further includes the step of 18-MC blocking $\alpha 3 \beta 4$ nicotinic receptors in the habenulo-interpeduncular pathway and the basolateral amygdala. The 18-MC can further inhibit enzymes CYP2C9, CYP2C19, CYP2C8, CYP2E1, and CYP3A4.

The present invention also provides for the composition of a metabolite of 18-MC salt and a method of treating substance use disorders by administering an effective amount of a metabolite of 18-MC salt in a pharmaceutical carrier to an individual and preventing substance abuse. Example 7 shows that metabolites M4 and M5 can bind to the $\alpha 3 \beta 4$ receptors, although with faster dissociation rates than 18-MC, and M5 has a slower association rate. M4 can pre-bind to inhibit nAChRs in the absence or presence of agonist. Metabolites M4 and M5 retain some of the activity of 18-MC, though with reduced potency.

Figure 17:
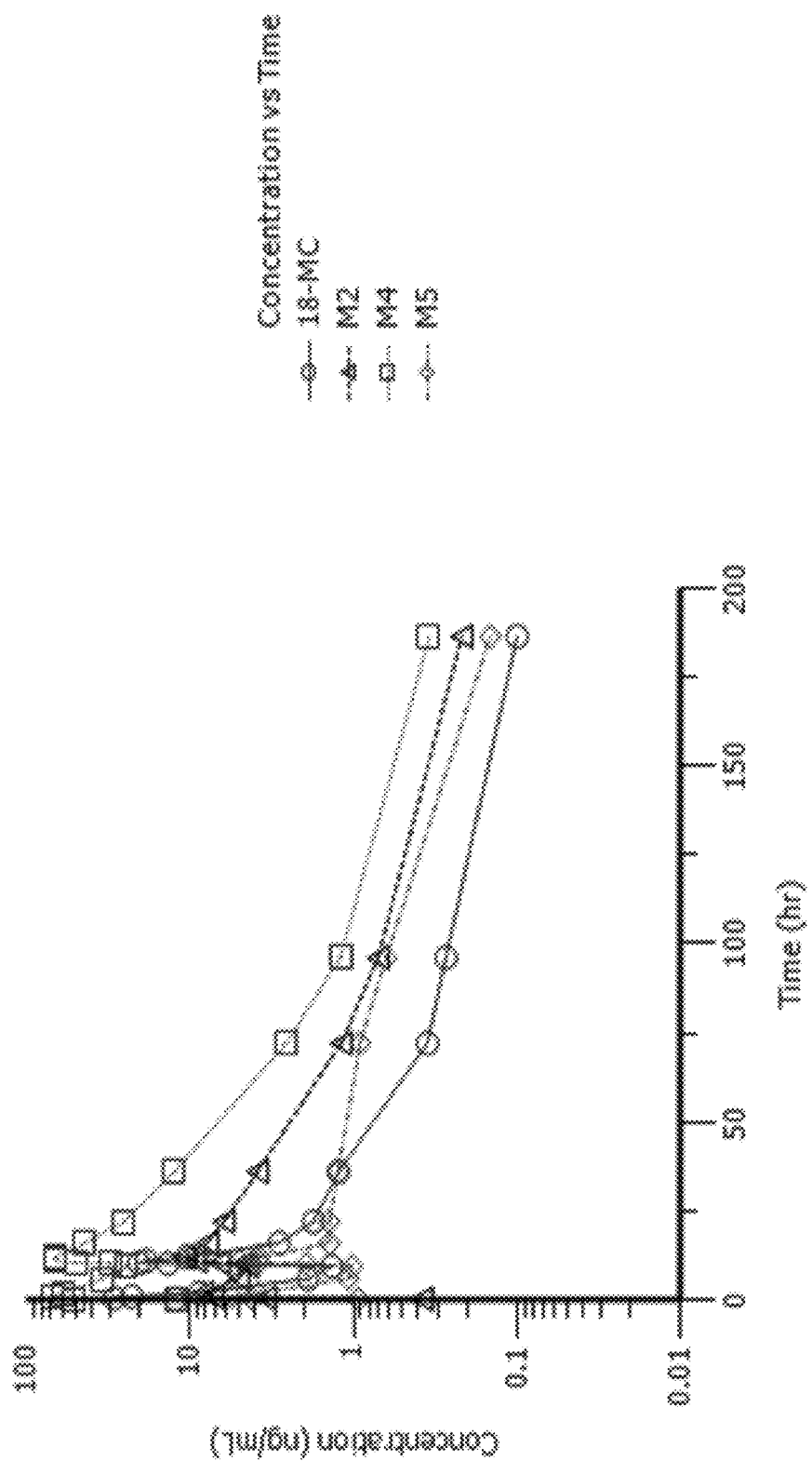
FIG. 17 is a graph of the average concentrations of 18-MC, M2, M4 and M5 (log-linear), cohort B (4 mg at 0 and +10 hours) in humans.
Figure 18A:
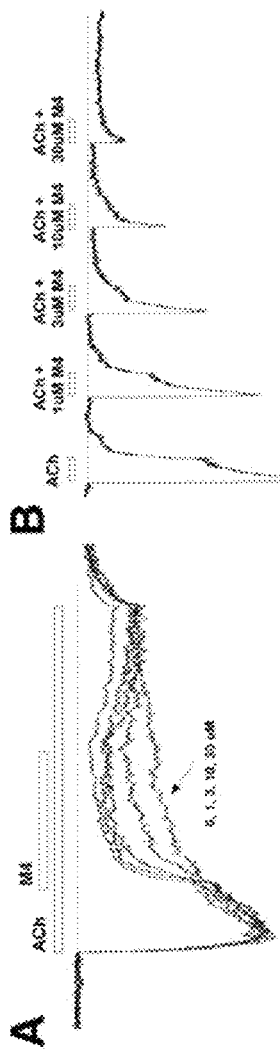
FIG. 18A is a concentration response curve for M4.
Figure 18B:
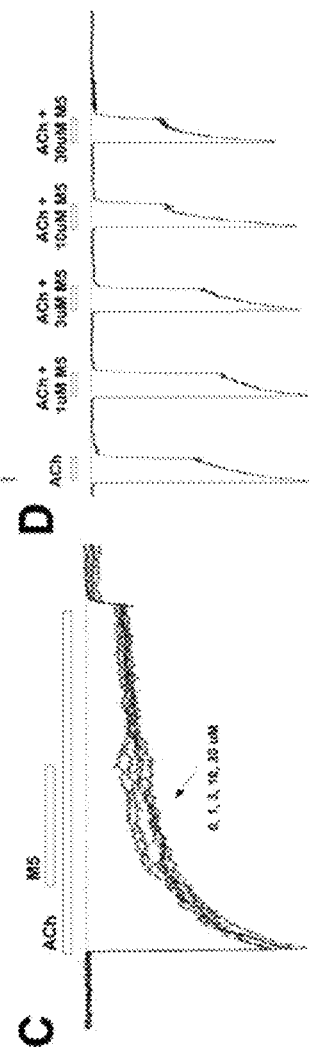
FIG. 18B is a concentration response curve for M4.
Figure 18C:
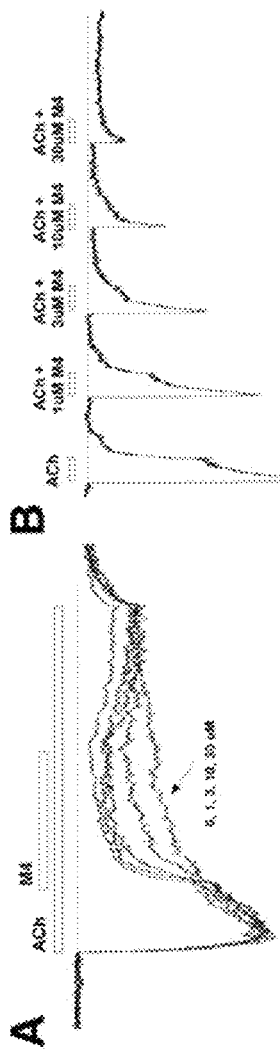
FIG. 18C is concentration response curve for M5.
Figure 18D:
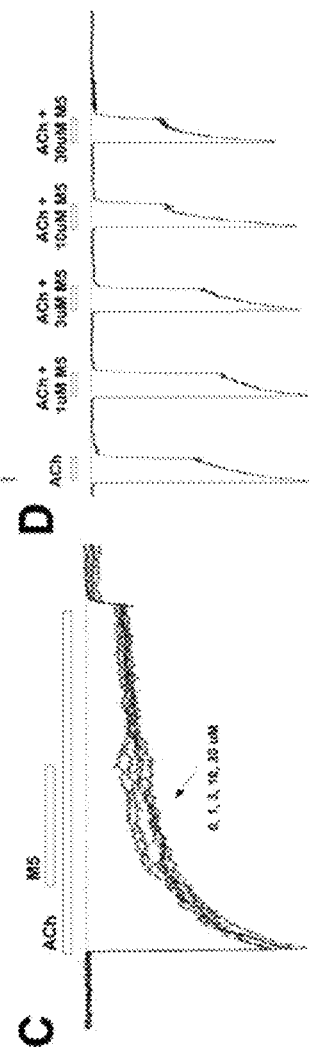
FIG. 18D is a concentration response curve for M5.
Figure 18E:
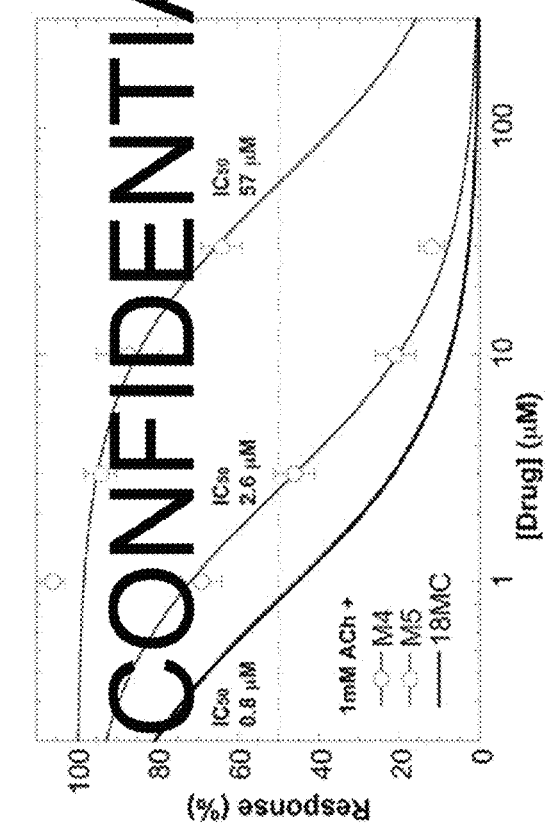
FIG. 18E is a dose response curve for M4, M5, and 18MC.
Figures 19A, 19B:
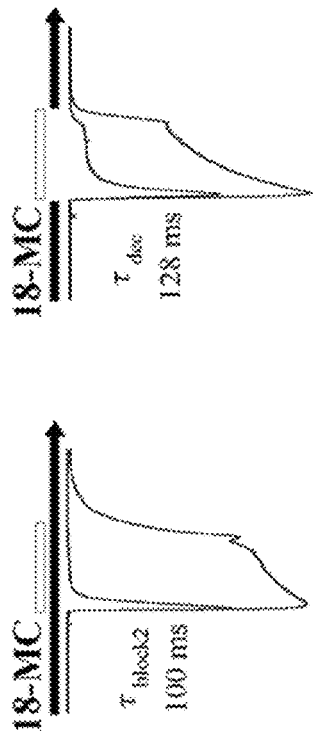
FIGS. 19A and 19B are graphs showing 18-MC pre-binds in the absence of ACh and continues to accelerate ACh–evoked current decay for some time after removal.
Figures 20A, 20B, 20C, 20D:
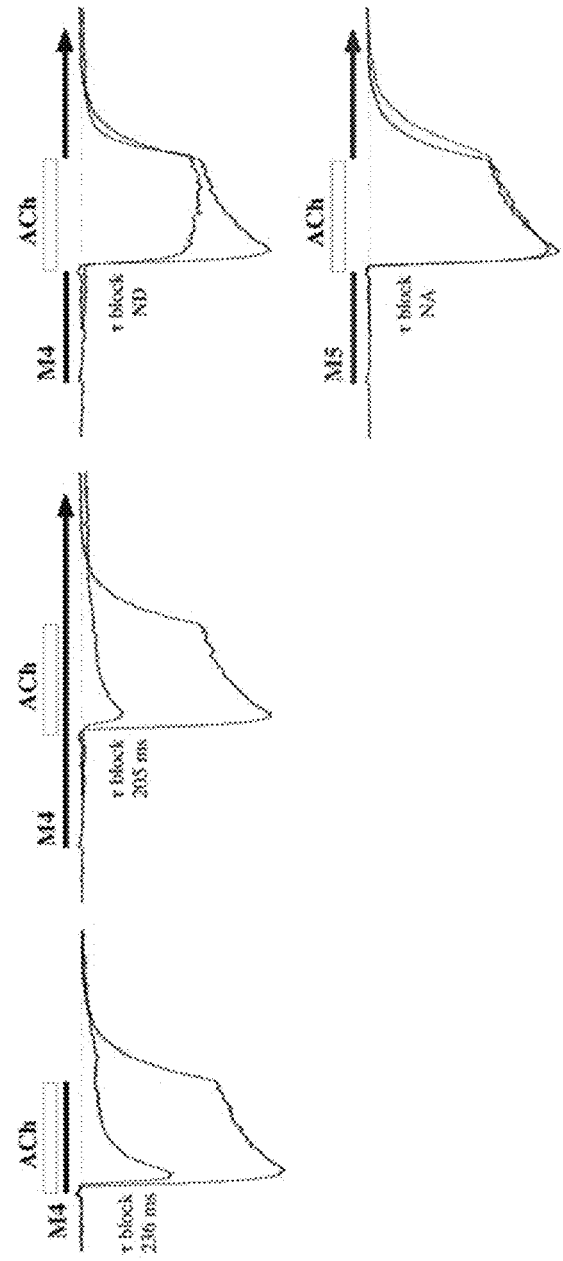
FIGS. 20A-20D are graphs showing M4 and M5 binding profiles.
Figure 21A:
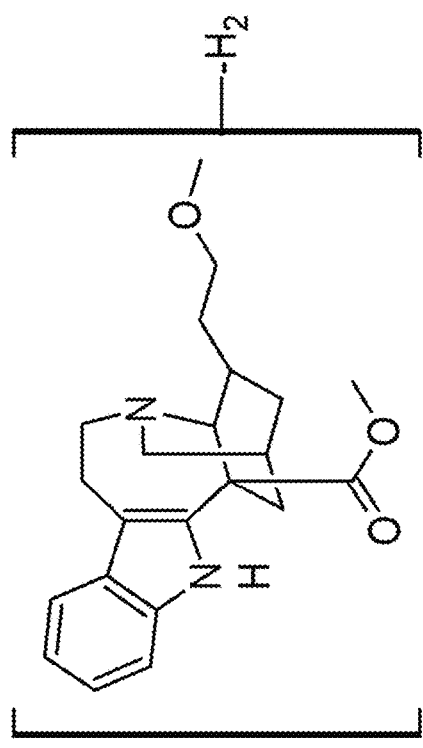
FIG. 21A is the chemical structure of M4.
Figure 21B:
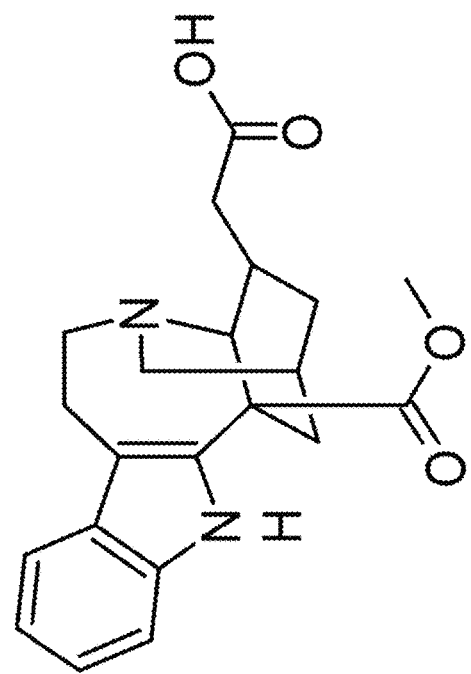
FIG. 21B is the chemical structure of M5.
Figure 21C:
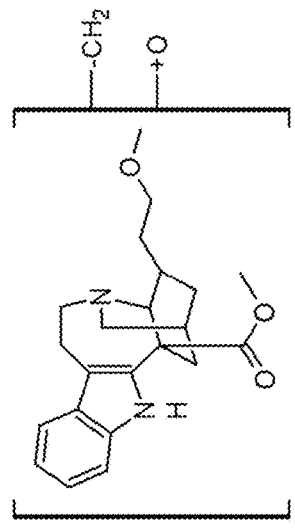
FIG. 21C is the chemical structure of M1.
Figure 21D:
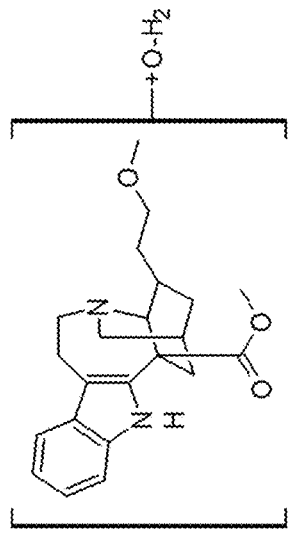
FIG. 21D is the chemical structure of M2.
Figure 21E:
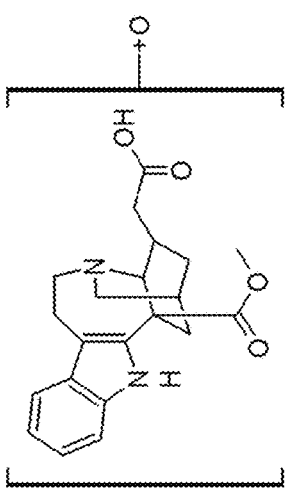
FIG. 21E is the chemical structure of M3.
Figure 21F:
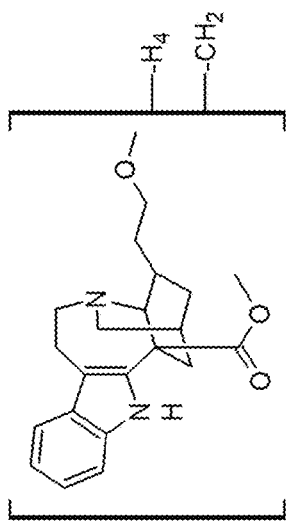
FIG. 21F is the chemical structure of M6 and M7.
Figure 21G:
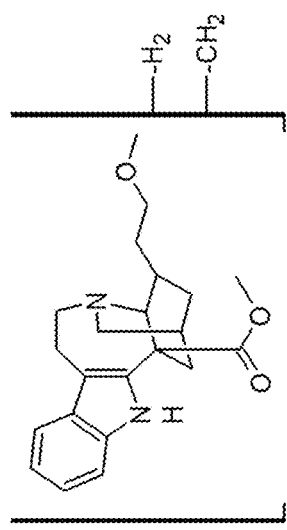
FIG. 21G is the chemical structure of M8 and M9.
Figure 21H:
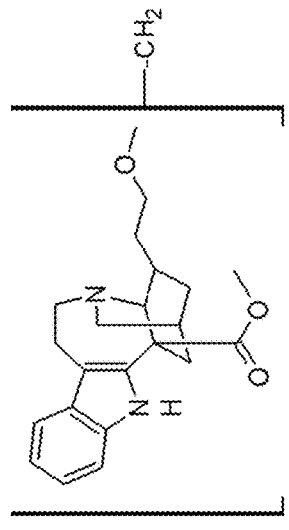
FIG. 21H is the chemical structure of M10.
Figure 21I:
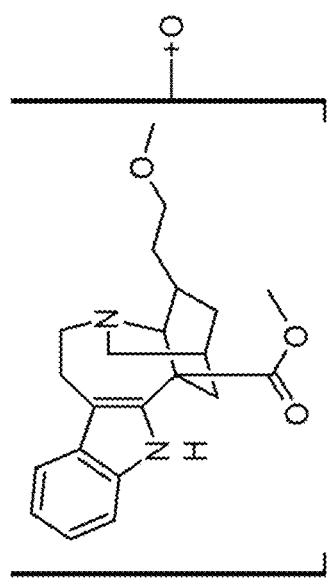
FIG. 21I is the chemical structure of P1.
Figure 21J:
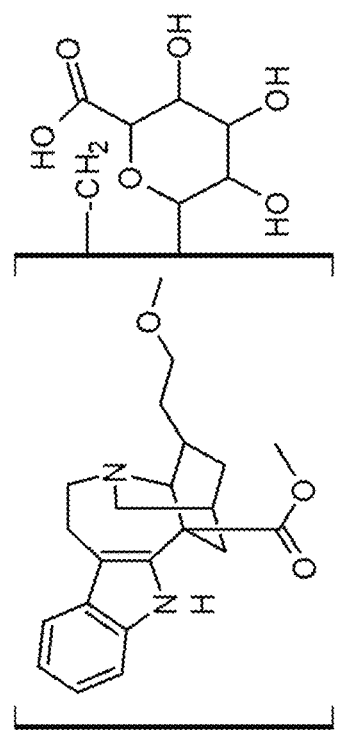
FIG. 21J is the chemical structure of P2 and P3.
Figure 22:
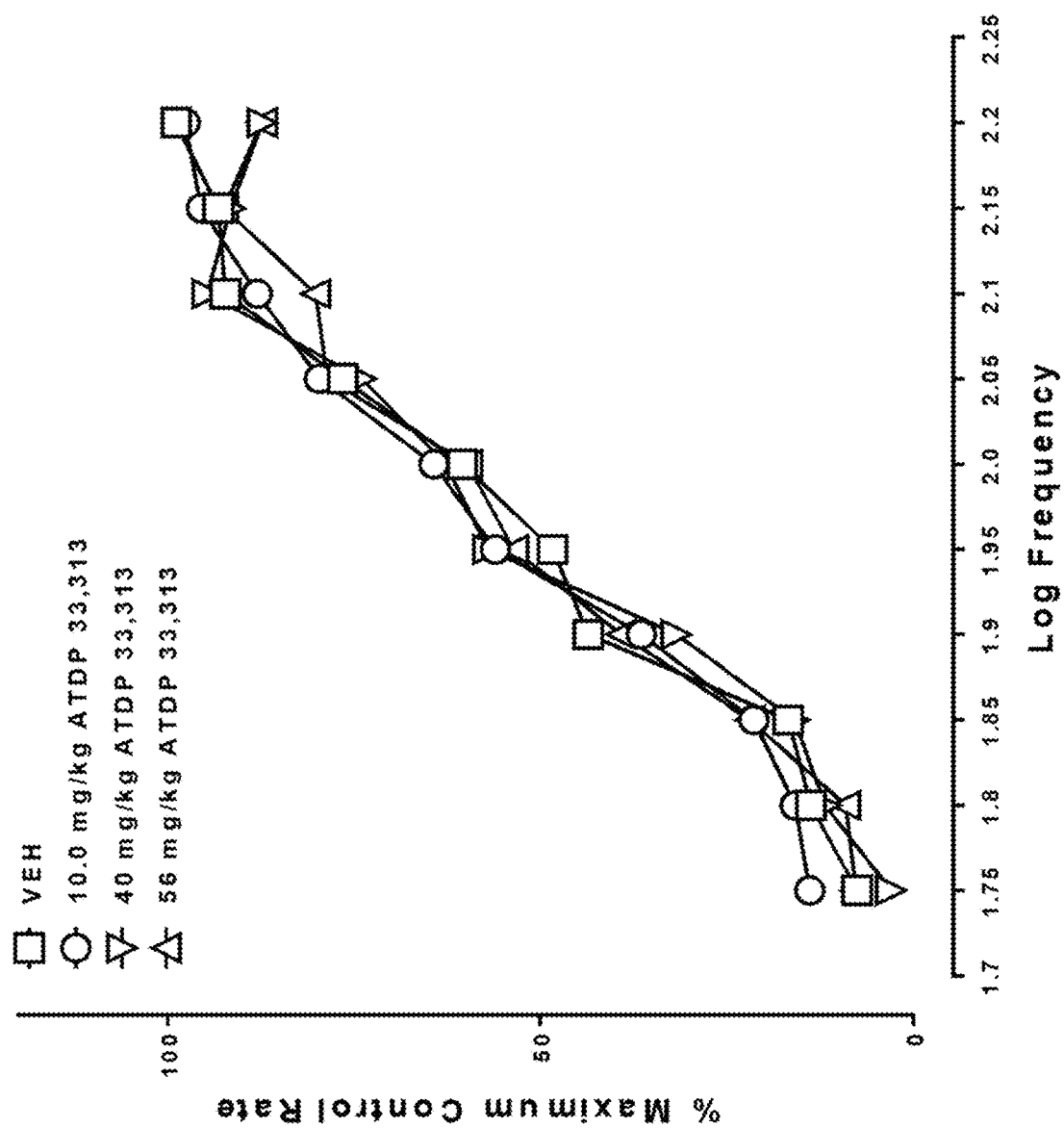
FIG. 22 is a graph of the effects of MC-18 on ICSS in rats.

The present invention further provides for a composition having the binding profile shown in FIG. 2, a composition having an action potential duration in rabbit cardiac Purkinje fibers shown in FIG. 13, a composition having a pharmacokinetic profiles of parent and a metabolite in human plasma shown in FIG. 17, a composition having an $IC_{50}$ profiles of parent and one or more metabolites as shown in FIG. 18E, a composition having an alpha3-beta4 nicotinic cholinergic receptor patch clamp assay profile as shown in FIGS. 19A and 19B, a composition having a human metabolite alpha3-beta4 nicotinic cholinergic receptor patch clamp assay profile as shown in any of FIGS. 20A, 20B, 20C and 20D, and a composition having an ICSS study profile in rats as shown in any of FIG. 22, 23, or 24.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

Example 1

Nonclinical Pharmacology

The pharmacological activity of 18-MC was tested by whole-cell patch clamp recording of HEK 293 cells expressing recombinant α3β4 nACh receptors, using methods previously described by Pace et al (2004). Application of 1 mM ACh produced a large, inward, desensitizing current with an $IC_{50}$ of 18-MC, 0.8 μM.

In vitro and in vivo experiments were conducted to gain understanding about the functional activity of 18-MC. The mechanism of action was examined in electrophysiology studies and the in vivo activity of 18-MC HCl was assessed using a rat model of cocaine self-administration.

Below is a description of the studies performed.

A representative tracing for 18-MC receptor binding is shown in FIG. 2. Application of 1 mM ACh produced a large, inward, desensitizing current similar to that described previously. The results were consistent with previous studies (Glick et al, 1996; Pace et al, 2004) showing that 18-MC potently inhibited α3β4 nACh receptors.

Intraperitoneal Administration of 18-MC HCl Inhibits Rat Cocaine Self-Administration 18-MC HCl was assessed in a rat cocaine addiction model (Glick et al, 1996). 18-MC dose-dependently decreased cocaine self-administration in rats (FIG. 3). Note that these effects were selective, in that the same doses of 18-MC HCl did not affect responding for water, a non-drug reinforcer. Female Sprague-Dawley rats weighing approximately 250 g were trained to self-administer cocaine hydrochloride (0.4 mg/kg per infusion) or water (0.01 ml per bar-press) during daily one hour test sessions based on a fixed ratio schedule of FR=3. 18-MC HCl (10-40 mg/kg, i.p.) administered 15 minutes prior to the session significantly decreased responding for cocaine but had no effect on responding for water. Each data point is the mean (±S.E.M) from 4-8 rats. All tested doses of 18-MC HCl had significant effects (ANOVA and t-tests, *=p<0.05-0.001).

Relationship of Inhibition of Rat Cocaine Self-Administration and 18-MC Plasma Concentrations The relationship between in vivo efficacy and plasma drug exposure was investigated in rats trained to self-administer cocaine. Trained animals given a single oral dose of 18-MC HCl were placed one hour later into the operant chamber for another hour to record the volume of self-administered cocaine. Blood samples were collected immediately after the one hour session in the operant chamber from the arterial catheter. Repeat measurements for cocaine self-administration were collected at 25, 49, 73, 97, 121, 146 hours following the single oral dose of 18-MC HCl. The inhibitory effects of different 18-MC HCl doses measured over a 7 day period are shown in FIG. 4. Following stable acquisition of cocaine self-administration (0.32 mg/kg/infusion), 18-MC HCl (or vehicle) was administered p.o. and responding for cocaine was measured at 1 hour (0 days), and subsequently, for 6 days post-treatment. Significant differences from vehicle-treated animals were either p<0.01 (indicated as **) or p<0.05 (indicated as *).

Cocaine self-administration 1 hour post dose was inhibited by 18-MC HCl in a dose-dependent manner. The inhibitory effect of 18-MC HCl was, however, highly variable among animals. The inhibitory activity gradually reversed over time and cocaine self-administration was fully restored to baseline values by Day 6 (146 hours post-dose). Inhibition of cocaine self-administration measured at 1 hour post-dose occurred in a dose-dependent manner; cocaine self-administration was inhibited by 50% after the administration of 120 mg/kg and by 82% after dosing with 800 mg/kg dose (FIGURE 5). Significant difference from vehicle-treated group (0 mg/kg on X axis) was p<0.01 (indicated as **) by one-way ANOVA.

The plasma concentration of 18-MC was highly variable among individual animals (FIG. 6). The inhibition of cocaine self-administration by 18-MC (at 1 hour post dose) was related to its plasma concentration (at approximately 2 hours post dose) (FIG. 7). Each data point in FIG. 7 represents a single animal with its self-administration data were collected at 1 hour post-dose for an hour and its 18-MC plasma concentration in blood samples collected immediately after the recording session at approximately 2 hours post-dose. Dotted lines are the upper and lower bounds of the 95% confidence interval (−0.8187 to −0.1395). The data conformed to a second-order fit with $R^2=0.324$, p=0.0137. This observation suggests that plasma drug concentration can be a surrogate predictive of the central effect of 18-MC, as greater efficacy was seen at higher plasma concentrations than at lower concentrations.

Repeated dosing with 18-MC HCl (600 mg/kg/day) over 5 consecutive days 1 hour prior to the self-administration session did not result in greater inhibition of cocaine self-administration (FIG. 8). Significant difference from baseline responding was p<0.01 (as indicated by **). Instead, the inhibitory effects on the second to fifth day of dosing were less than the inhibitory effect seen with the first dose. On average, the plasma concentration of 18-MC at 2 hours post-dose was lower on the last day of dosing compared to the first day (TABLE 1). Blood samples were collected from animals immediately after their cocaine self-administration at approximately 2 hours post dose in the first day of dosing (Day 0), and the last day of dosing (Day 4). Pre-dose samples were collected about 1 hour prior to the last dose of 18-MC HCl (on Day 4).

TABLE 1

Plasma 18-MC concentration in individual animals on first and last day of dosing in a 5-day study

| Dose Day | PK Sampling Time | Animal I.D. | | | | | | Plasma 18-MC Concentration (ng/mL) | |
|---|---|---|---|---|---|---|---|---|---|
| | | 89224 | 89225 | 89228 | 89232 | 89237 | 89243 | Average | SEM |
| 0 | Post dose | 3,450 | 12,600 | 11,300 | 13,900 | 14,200 | 13,200 | 11,442 | 1653.0 |
| 4 | Pre dose | 3,840 | 1,680 | 3,020 | — | 2,720 | 3,730 | 2,998 | 391.1 |
| 4 | Post dose | 9,030 | 3,760 | 8,040 | — | 10,500 | 6,290 | 7,524 | 1163.6 |

All of the available PK data points collected on the first 3 days following dosing were analyzed with their corresponding self-administration values for individual animals. The analysis showed a second-order fit between inhibition of cocaine self-administration and 18-MC plasma concentration with $R^2=0.425$ and $p<0.0001$ (FIG. 9). Animals were administered a single oral dose of 18-MC HCl and the volumes of self-administered cocaine were recorded at 1, 25, 49, 73, 97, 121, 146 hours post dose. A blood sample was collected after each recording session. All data point represents the cocaine self-administration volume and 18-MC plasma concentration in blood samples collected immediately after that particular recording session. Data points with missing 18-MC plasma concentrations were excluded from the analysis. Dotted lines are the upper and lower bounds of the 95% confidence interval (−0.7742 to −0.4845).

18-MC Blocks Sensitized Dopamine Response to Cocaine in Rat Nucleus Accumbens

Because dopamine release in the nucleus accumbens (NAC) has been implicated in the reinforcing actions of drugs of abuse, the effects of systemic 18-MC HCl (40 mg/kg) pretreatment (19 hours beforehand) on the acute and sensitized dopamine responses in the nucleus accumbens shell to cocaine administration were examined (Szumlinski et al, 2000). 18-MC HCl pretreatment had little effect on the acute response to cocaine but abolished the sensitized dopamine response to cocaine.

The results indicate that 18-MC HCl can reverse the sensitized dopaminergic response to drugs, which is believed to be the neurochemical substrate of drug craving (FIG. 10). These results are consistent with evidence that 18-MC decreases the rewarding effects of drugs. Rats were implanted with a microdialysis guide cannula over the shell of the NAC. Rats received daily injections of cocaine (15 mg/kg, i.p.) or saline for 5 days. Following 2 weeks of withdrawal, rats were pretreated with either 18-MC HCl (40 mg/kg, i.p.) or vehicle. The next day a microdialysis experiment was performed and the effects of cocaine (20 mg/kg, i.p.) were assessed. The samples were analyzed by HPLC-EC. N=5-7/group. (Vehicle vs. 18-MC pretreated groups, *=p<0.05)

18-MC HCl Blocks Context-Induced Reinstatement of Cocaine Seeking (a "Cravings" Model)

Diminishing drug craving is considered to be a critical component of any treatment of addiction. Several models of craving have been proposed to measure the tendency of rats to respond to stimuli associated with the self-administration of a drug. Polston et al (2012) used prolonged music cues to alter the context of drug self-administration (FIG. 11). Animals were trained to self-administer cocaine in the presence of music. Self-administration behavior was then extinguished over several days in the absence of music. Subsequently, under extinction conditions, when music was re-introduced, it reinstated cocaine seeking behavior (i.e., responding on the cocaine-paired lever). 18-MC HCl (40 mg/kg, i.p.) blocked the reinstatement effect of cues associated with cocaine self-administration.

Data depicted as mean cocaine infusions (±SEM) during self-administration trials, and theoretical infusions earned during extinction sessions. Active lever presses (±SEM) during the reinstatement test session are plotted accordingly with the right x-axis. Animals were on an FR1 schedule of reinforcement on days 1-12 and changed to an FR3 schedule for the remainder of the experiment. Animals in the Music condition made significantly more responses on the drug-paired lever on the reinstatement test day (Test) than animals in the NMCond and NMTest groups. Additionally, significant differences were observed on the first day of extinction (Ext 1); animals that had not been conditioned with music during self-administration (NMCond) made significantly more responses than animals that had been trained with music. * $p<0.05$, *** $p<0.001$.

Example 2

Secondary Pharmacodynamics

In Vitro Radio-Ligand Receptor and Enzyme Assays

The binding potential of 18-MC with 64 neurotransmitter-related binding sites was evaluated (TABLE 2). 18-MC at 100 nM concentration had no binding activity to any of the receptors assayed. Binding was seen only to the adrenergic alpha-1 receptor, Mu opioid receptor, and sodium site 2 channel ligands at 10 µM, which is several orders of magnitude greater than the expected human plasma concentration of unbound 18-MC.

TABLE 2

Binding sites tested with 18-MC HCl in the radio-ligand assays

NEUROTRANSMITTER RELATED

Adenosine, Non-selective
Adrenergic, Alpha 1, Non-selective
Adrenergic, Alpha 2, Non-selective
Adrenergic, Beta 1
Cannabinoid, CB1
Cannabinoid, CB2
Dopamine, D4.2
GABA A, Agonist Site
GABA A, BDZ, alpha 1 site
GABA-B
Glutamate, AMPA Site (Ionotropic)
Glutamate, Kainate Site (Ionotropic)
Glutamate, NMDA Agonist Site (Ionotropic)
Glutamate, NMDA, Phencyclidine Site (Ionotropic)
Glutamate, mGluR1 (Metabotropic)
Glutamate, mGluR5 (Metabotropic)
Glutamate, NMDA, Glycine (Strychnine-insen)
Glycine, Strychnine-sensitive
Histamine, H1
Histamine, H2

TABLE 2-continued

Binding sites tested with 18-MC HCl in the radio-ligand assays

Histamine, H3
Muscarinic, M1
Muscarinic, M2
Muscarinic, Non-selective, Peripheral
Nicotinic, Muscle (a-BnTx sensitive)
Nicotinic, Neuronal (a-BnTx insensitive)
Opioid, Kappa 1
Opioid, Mu
STEROIDS Estrogen NR3AI
Glucocorticoid
Testosterone (cytosolic)
ION CHANNELS Calcium Channel, Type L (Benzothiazepine Site)
Calcium Channel, Type L (Dihydropyridine Site)
Calcium Channel, Type N
Potassium Channel, ATP-Sensitive Potassium Channel,
Ca2+ Act., VI
Sodium, Site 2
SECOND MESSENGERS Nitric Oxide, NOS (Neuronal-Binding)
PROSTAGLANDINS Leukotriene, LTB4 (BLT)
Leukotriene, LTD4 (CysLT1)
Thromboxane A2
GROWTH FACTORS/HORMONES Corticotropin Releasing Factor, Non-selective
Oxytocin
Platelet Activating Factor, PAF
Thyrotropin Releasing Hormone, TRH
BRAIN/GUT PEPTIDES Angiotensin II, AT1
Angiotensin II, AT2
Bradykinin, BK2
Cholecystokinin, CCK1 (CCKA)
Cholecystokinin, CCK2 (CCKB)
Endothelin, ET-A
Endothelin, ET-B
Galanin, Non-Selective
Neurokinin, NK1
Neurokinin, NK2 (NKA)
Neurokinin, NK3 (NKB)
Vasoactive Intestinal Peptide, Non-selective
Vasopressin 1
ENZYMES Decarboxylase, Glutamic Acid
Esterase, Acetylcholine
Oxidase, MAO-A, Peripheral
Oxidase, MAO-B, Peripheral
Transferase, Choline Acetyl Example 3

Safety Pharmacology

To assess the effects of 18-MC HCl upon the central nervous, respiratory, and cardiovascular systems, a series of studies were conducted according to FDA and ICH guidance. In vitro studies (hERG ionic conductance and action potential duration in rabbit cardiac purkinje fibers) were performed to evaluate potential effects upon cardiac electrophysiology, and in vivo studies were performed in the rat and monkey to evaluate effects upon behavior and pulmonary and cardiovascular function. As no sex-specific effects were anticipated based upon prior data, the in vivo studies employed only one sex (males). The in vitro rabbit purkinje and in vivo safety pharmacology studies were conducted under GLP regulations.

In Vitro Safety Pharmacology

In Vitro hERG Channel Inhibition Assay

Figure 12:
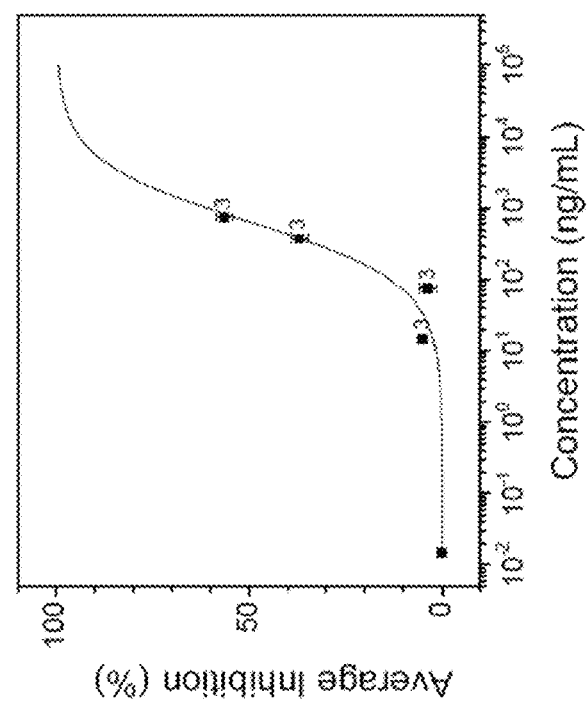
FIG. 12 is a graph of hERG potassium channel inhibition by 18-MC.

The potential for 18-MC to inhibit the hERG potassium channel was evaluated in a stably transfected Chinese Hamster Ovary (CHO) cell line expressing hERG mRNA (FIG. 12). The $IC_{50}$ was 1.46 µM. Since this result is considered a moderate risk for QT prolongation, a more sensitive test (which measures action potential depolarization in whole Purkinje fibers isolated from rabbit heart) was performed. Cells were voltage clamped at a holding potential of −80 mV. The hERG current was then activated by a depolarizing step (−50 mV for 300 ms) and repeated every 12 s. 18-MC was prepared from 10 mM methanol stock solutions. The hERG current inhibition was calculated from the average of 3 separate recordings. The $IC_{50}$ is 1.6 µM.

Action Potential Duration (APD) in Rabbit Cardiac Purkinje Fibers

The in vitro effect of 18-MC on the cardiac action potential was evaluated in isolated rabbit Purkinje fibers (FIG. 13). FIG. 13 shows superimposed records before (control) and after equilibration of the test article (0.3, 1, 3 and 10 µM 18-MC) using a 1 second base cycle length (BCL). Not shown was a positive control dl-Sotalol (50 µM) significantly prolonged (~40%) $APD_{60}$ and $APD_{90}$. Fibers with resting potentials more negative than −80 mV and normal action potential morphology ($APD_{90} \geq 150$ ms) were used in the study. Fibers were stimulated continuously at BCL of 1 second for at least 5 minutes. At the end of this period, baseline control APD rate dependence was measured using stimulus pulse trains consisting of approximately 50 pulses at BCL of 1 and 0.5 seconds. After returning to BCL of 1 second, 18-MC (or dl-sotalol) at the lowest concentration was applied for at least 20 minutes to allow equilibration, and the stimulus trains repeated. The entire sequence (~20 minutes of equilibration followed by stimulus trains at decreasing BCL) was repeated at cumulatively increased 18-MC concentration. The average responses from the last five recorded action potentials from each stimulus train were analyzed for each test condition.

Electrophysiological recordings were performed with four nominal concentrations of 18-MC (0.3, 1, 3, and 10 µM) added sequentially to four preparations at two stimulus intervals (basic cycle lengths of 1s and 0.5s). The effects of 18-MC on action potential parameters were compared to time-matched vehicle control sequences. 18-MC did not prolong the QT interval at any concentration tested. However, at 3 µM, 18-MC induced statistically significant ($p<0.05$) shortening of the action potential duration $(APD)_{60}$ at 1 second base cycle length (BCL). 18-MC at 10 µM induced statistically significant ($P<0.05$) shortening of $APD_{60}$ at 0.5 and 1s BCL. 18-MC did not induce significant changes (at any of the concentrations tested) in resting membrane potential (RMP), action potential amplitude (APA) or $V_{max}$ at two stimulus intervals. In summary, in isolated rabbit Purkinje fibers, 18-MC did not prolong the QT interval, but at concentrations of 3 µM and 10 µM induced statistically significant shortening in action potential repolarization.

In Vivo Safety Pharmacology

Central Nervous System: Modified Irwin Test Following Oral Administration of 18-MC HCl to Sprague Dawley Rats The effects of orally administered 18-MC HCl on the gross behavioral, physiological, and neurological states were evaluated in two studies in Sprague Dawley rats using a modification of a primary observation test, the modified Irwin test.

A pilot dose finding study was performed in female rats receiving a single oral dose of 30-800 mg/kg 18-MC HCl in different formulations. Under the conditions of this study, the no-observed-effect level (NOEL) and no-observed-adverse-effect level (NOAEL) were considered to be 90 mg/kg and 400 mg/kg, respectively.

A second, definitive GLP study was performed in male rats receiving a single oral dose of 0, 200, 400 and 600 mg/kg 18-MC HCl. The objective of this study was to evaluate the effects of a single dose of 18-MC HCl, orally administered, on the gross behavioral, physiological, and neurological state of male Sprague Dawley rats using a modification of a primary observation test, specifically the Irwin test. Only male rats were utilized in the assay, as no significant sex-specific effects have been noted in prior toxicology studies.

Vehicle (5% dextrose, pH 3) or 18-MC HCl in the vehicle (adjusted to pH 3) was administered as a single oral dose by gavage at 0, 200, 400, or 600 mg/kg, respectively, to 4 groups (Groups 1 through 4) of 6 male Sprague Dawley rats/group. The dose volume for all groups was 20 mL/kg. Observations for the Irwin test were performed pre-dose (on the day of dosing) and at approximately (±5 minutes) 30, 90, 150, and 240 minutes post-dosing. Body temperature was measured and recorded during each Irwin observation period.

Neurobehavioral findings judged as minimal in severity and generally consistent with the intended pharmacological activity of the test article, a central α3β4 nicotinic receptor antagonist that attenuates dopaminergic transmission (Szumlinski et. al., 2000), were noted as early as 30 minutes post-administration. As shown in TABLE 3, the predominant observations (ones that occurred in at least half the animals in the mid- and/or high-dose groups at a given time point) were an increased incidence of passivity and abnormal gait (waddling and/or walking low on limbs). Other observations consisted of decreased locomotor activity, decreased alertness, slower respiration rate, decreased cutaneous blood flow, and/or increased pupil diameter. The findings appeared to be dose-dependent noted primarily in animals of the higher dose groups in which increased frequency and occurrence corresponded to increased dose. Observations at the 200 mg/kg dose were limited to isolated occurrences (one animal at a given time point) of passivity, increased touch response, reduced locomotor activity, and/or increased pupil diameter. The time of peak effect of the observations appeared to occur between 90 and 150 minutes post-dosing. A dose-dependent decrease in body temperature was also noted (mean decreases from pre-dose values of up to 1.5, 2.3, and 2.3° C. in the 200, 400, and 600 mg/kg groups, respectively) and peaked at approximately 90 minutes post-dosing. By 240 minutes post-dose, the number of animals with observations and the frequency and severity of observations was reduced in 18-MC HCl-treated animals relative to that seen at earlier time points.

TABLE 3

Summary of Irwin test parameter occurrences
Total Occurrence(s)/No. of Males (Within Observation Period$^a$)

| Finding | Group 1 Control | Group 2 200 mg/kg | Group 3 400 mg/kg | Group 4 600 mg/kg |
|---|---|---|---|---|
| Decreased locomotor activity | | 1/6 (90) | 2/6 (90, 150) | 2/6 (30, 90, 150, 240) |
| Passivity | 1/6 (90, 240) | 1/6 (30, 90, 150, 240) | 1/6 (30, 90, 240) 3/6 (150) | 1/6 (pre) 2/6 (240) 3/6 (30, 90) 4/6 (150) |
| Decreased alertness | | | 1/6 (30) | 1/6 (150, 240) 2/6 (30, 90) |
| Slower respiration rate | | | 1/6 (90, 150, 240) | 1/6 (90, 150) |
| Abnormal gait (waddling) | | | 1/6 (30, 150) 2/6 (90) | 1/6 (240) 2/6 (30) 3/6 (150) 4/6 (90) |
| Abnormal gait (walking low on limbs) | | | 1/6 (90) | 1/6 (30) |
| Increased touch response | | 1/6 (pre, 30) | 1/6 (pre) | |
| Increased pupil diameter | | 1/6 (30) | 1/6 (150) 2/6 (30, 90) | 1/6 (90) |
| Decreased cutaneous blood flow | | | | 1/6 (30, 90, 150) |
| Diarrhea | | | | 1/6 (240) |

$^a$Observation periods include prior to dosing; 30, 90, 150, and 240 minutes post-dosing In conclusion, oral administration of 18-MC HCl in male Sprague Dawley rats was associated with dose-dependent neurobehavioral observations generally consistent with its intended pharmacological activity. The effects were predominantly noted at doses ≥400 mg/kg and peaked 90-150 minutes post-dosing, subsiding in occurrence by 240 minutes post-administration.

Cardiovascular and Respiratory System: Radiotelemetry Assessment Following Nasogastric Administration of 18-MC HCl to Conscious Cynomolgus Monkeys The potential acute effects of 18-MC HCl were evaluated in conscious radiotelemetry-instrumented male cynomolgus monkeys following nasogastric dosing of 0, 30, 90 or 270 mg/kg in a GLP study. Animals were assigned in a latin-square cross-over design and received a single dose of 18-MC HCl between each wash-out period of approximately 7 days. Arterial blood pressure, heart rate, body temperature, lead II electrocardiogram (ECG), and respiratory parameters were recorded continuously for approximately 1 hour prior to administration of vehicle or 18-MC HCl through approximately 24 hours post-dosing. Clinical observations were performed at approximately 4 and 24 hours post-dosing.

Single oral administration of 18-MC HCl at doses of 30, 90, or 270 mg/kg to male radiotelemetry-implanted cynomolgus monkeys did not affect cardiovascular parameters (i.e. heart rate, blood pressure [systolic, diastolic, or mean arterial], pulse pressure, ECG waveform morphology, or ECG intervals [PR, QRS, RR, QT, or QTcB]), body temperature, or respiratory parameters (respiratory frequency, tidal volume, or minute volume). Emesis occurred in some of the animals dosed with 270 mg/kg 18-MC HCl. There were no other drug-related clinical findings. The NOEL on the cardiovascular and respiratory systems was 270 mg/kg 18-MC HCl, the highest dose tested.

Figure 14:
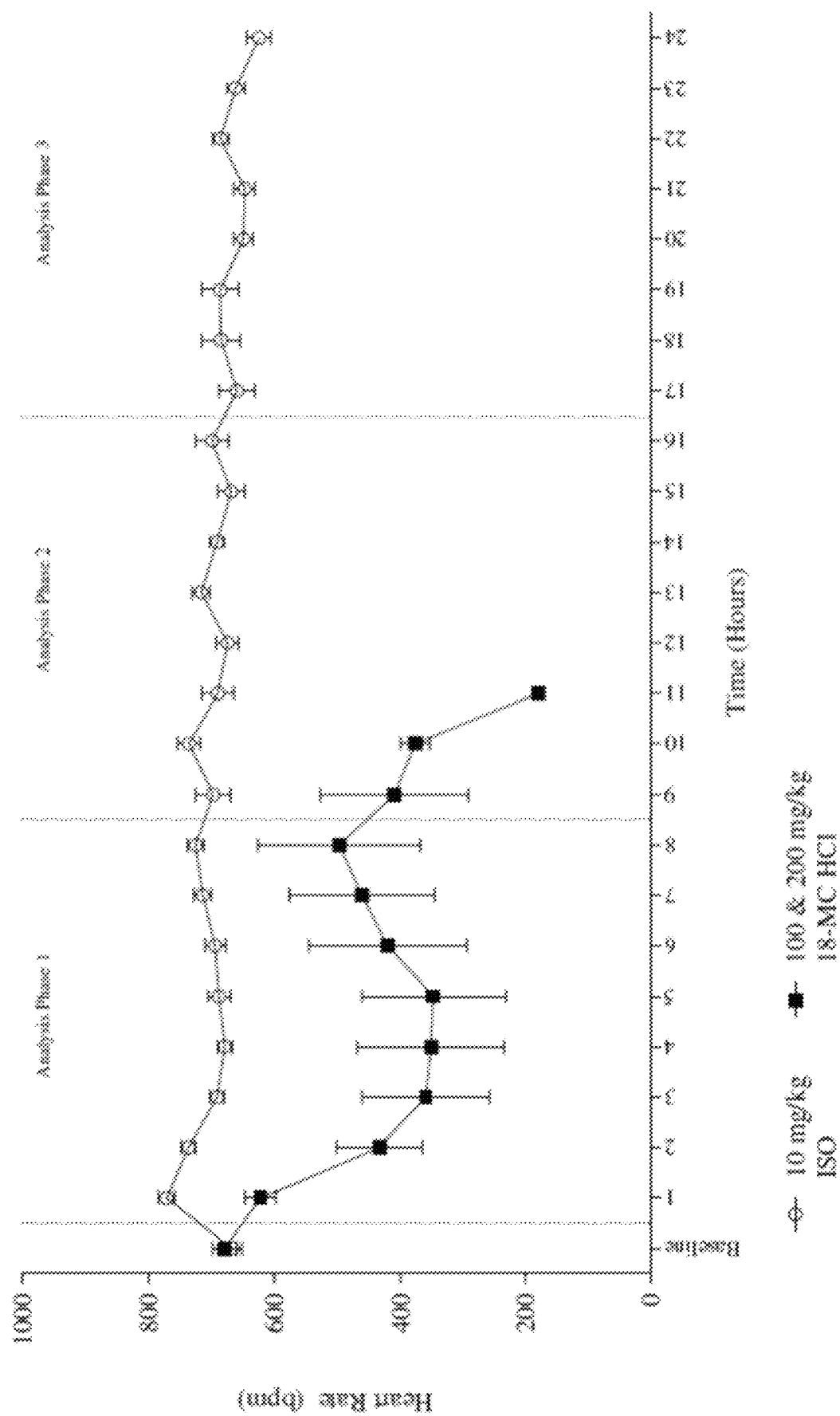
FIG. 14 is a graph of the change in mean heart rate after oral administration of 18-MC in CD-1 mice.
Figure 15:
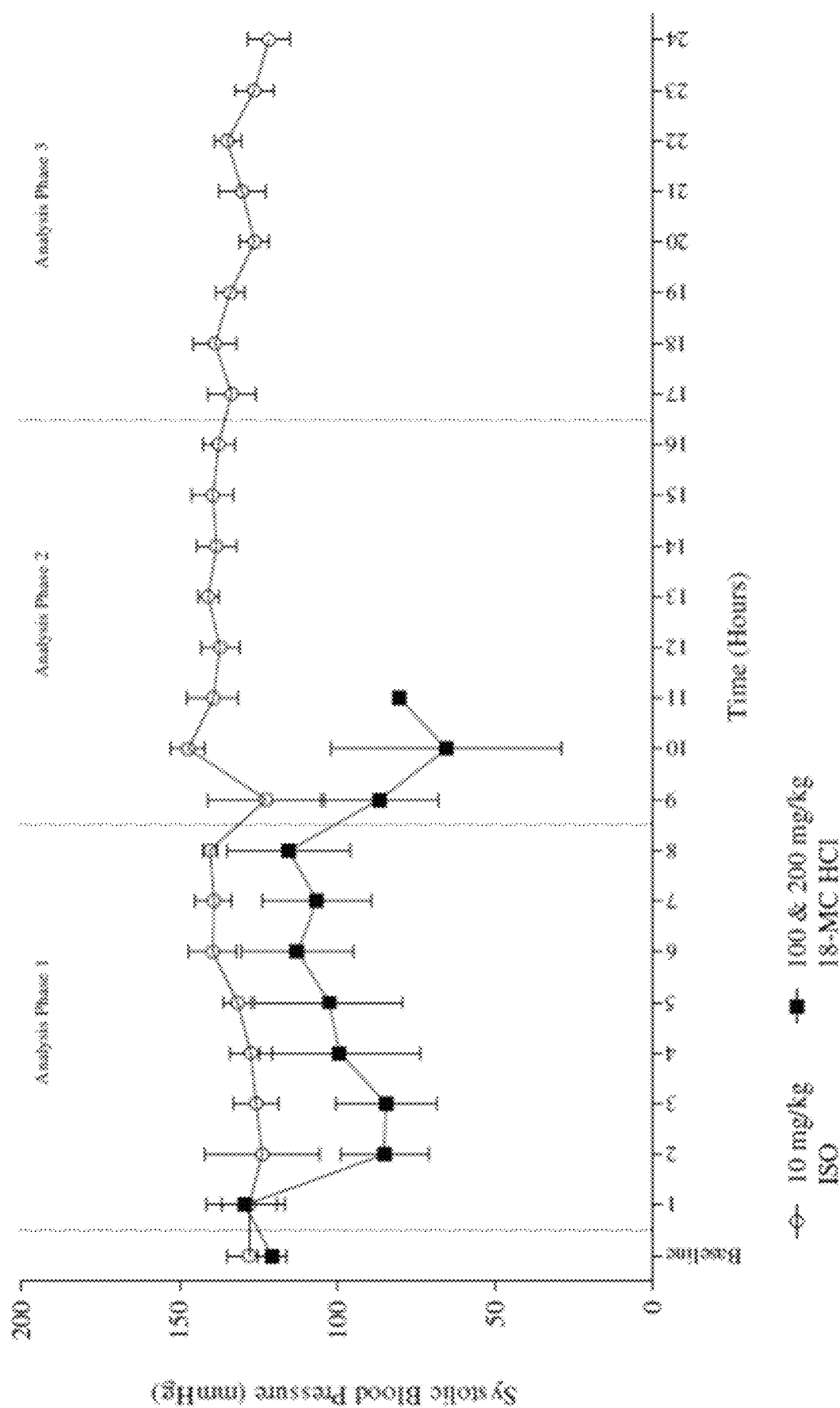
FIG. 15 is a graph of the change in mean systolic blood pressure after oral administration of 18-MC in CD-1 mice.
Figure 16:
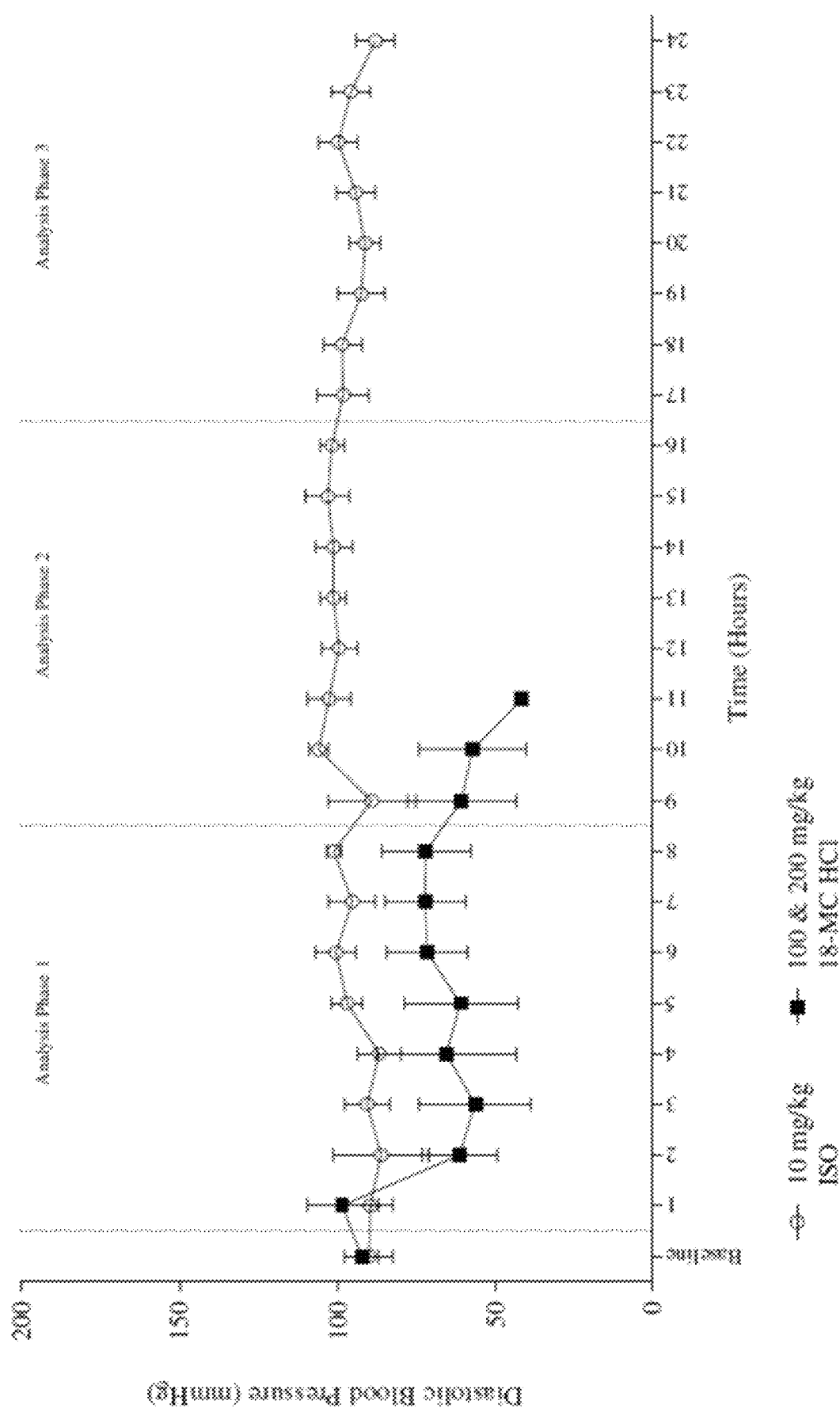
FIG. 16 is a graph of the change in mean diastolic blood pressure after oral administration of 18-MC in CD-1 mice.

Cardiovascular System: Radiotelemetry Assessment Following Oral Administration of 18-MC HCl to Conscious CD-1 Mice The potential acute effects of oral administration of 18-MC HCl on arterial blood pressure, heart rate, and body temperature was assessed in conscious male CD-1 mice by radiotelemetry-instrumentation in a non-GLP acute dosing study. Other studies showed lethality at lower oral doses of 18-MC HCl (100 mg/kg or less) in mice. The purpose of this study was to explore the physiological changes associated with mortality. Animals were implanted with a radiotelemetry transmitter in the peritoneal cavity with the catheter inserted in the femoral artery and the sensor tip positioned in the abdominal aorta. Six animals were each administered an oral dose of 100 mg/kg and, 8 hours later, 200 mg/kg 18-MC HCl in 5% dextrose (pH 3). Two of the 6 animals died after receiving the 100 mg/kg dose and all of the other animals died after the 200 mg/kg dose. Within one hour of dosing, average heart rate (FIG. 14) decreased about 50%, and significant decreases in systolic (FIG. 15) and diastolic blood pressure (FIG. 16). In addition, body temperature generally dropped at each collection time point, reaching a maximum difference from baseline at 120 minutes post-dose (average change up to 6.5° C.). Following administration of the 200 mg/kg dose, body temperature continued to drop (up to 10.5° C.) until all mice died (~12 hours post-dose). These changes in body temperature were considered test article-related and correlated to the observed changes in heart rate. Terminally, there was a further decrease in all of the parameters, with the rectal temperatures falling to as low as 22° C. before the mice died. Observed effects on behavior and activity included tremors, twitches, abnormal gait, lethargy, decreased motor activity, increased response to touch and startle, seizures, gasping and slow respirations, exophthalmia, and stupor. The peak effects occurred between 90 and 150 minutes after the oral administration of 18-MC HCl.

Lethal or near lethal oral doses of 18-MC HCl were associated with reductions in body temperature, heart rate and blood pressure. Differences from baseline were initially noted 1-2 hours post-administration and may reflect direct or indirect effects related to 18-MC HCl anticipated pharmacologic activity.

Based upon the results of this and the 2-week mouse toxicology study (where milder effects on body temperature were seen at a dose of 50 mg/kg), vital signs (including body temperature) can be closely monitored as part of the clinical trial. The effects seen in this study were not noted in the monkey cardiovascular safety pharmacology study suggesting the reductions observed may be species specific.

Example 4

Pharmacokinetics and Metabolism in Animals

The pharmacokinetics and metabolism of 18-MC HCl have been studied in a range of animal and human models. The key findings are summarized below.

18-MC is rapidly absorbed and distributed into the brain and fat tissues in rats dosed with 40 mg/kg p.o. or i.p. The estimated volume of distribution is 8 L/kg. 18-MC levels in fat were 4.2 µM and 2.5 µM at 2 hours and 24 hours, respectively. 18-MC HCl is extensively metabolized in vitro and in vivo with up to 13 metabolites identified. On oral administration, it appears that the major metabolites are either M4 or M5, depending on the animal species tested. M4 and M5 are the primary circulating drug species because they are present at proportions greater than 18-MC. 18-MC HCl has relatively low oral bioavailability in the rat (about 8% after the administration of 60 mg/kg). The oral bioavailability for total drug substance (AUC of 18-MC and its metabolites) is about 25% after the administration of 60 mg/kg in the rat. 18-MC HCl moderately inhibits CYP2C9 and CYP2C19 (<1.5 µM), and less so for CYP2C8, CYP2E1 and CYP3A4. 18-MC shows multi-compartmental elimination following oral administration. In the animal species tested its half-life is less than 2 hours at lower doses. At high doses a long elimination phase is evident (ranging from 9 to 20 hours in rats). 18-MC is highly protein bound (95-98%).

In Vitro Metabolite Profiling in Hepatocytes

This study evaluated in vitro metabolism of 18-MC HCl in hepatocytes prepared from livers of mouse, rat, dog, monkey and human. Following incubation of 18-MC HCl 10 µM in hepatocytes, 13 potential metabolites were found by liquid chromatography/mass spectrometry (LC/MS). The relative abundance of the metabolites was determined by the area under the curve of the peak heights. Metabolites with AUC greater than 10% of all drug-related material are considered major, and these are M2, M4, M5, M8, M9, and P2.

Exposure from the 14-Day Mouse Toxicokinetic Study

A 14-day oral gavage toxicity study of 18-MC HCl was conducted in CD-1 mice with a 14-day recovery period. The relative metabolite concentrations were determined from plasma samples obtained on the last day of dosing in the 25 mg/kg/day group of animals using a UPLC/MS/MS method. Major metabolites were identified as M2 and M4, followed by M8 and M9. The parent 18-MC exposure was less than 1% of the total drug related material. No significant sex differences were observed.

The 18-MC pharmacokinetic parameters demonstrated with an increase in the dose there was an increase in the 18-MC exposure. The parameters after the first and last day of dosing were similar and there was no consistent sex difference after 25 mg/kg but the female exposure appeared lower compared to the males with the higher doses.

Pharmacokinetics in 14-Day Monkey Study

In a 14-day 18-MC HCl toxicology study in the cynomolgus monkey with a 4-week recovery period, the relative metabolite concentrations were determined from plasma samples obtained on the last day of dosing (Day 14) in the high dose group. The animals received 400 mg/kg on Day 1 and thereafter 300 mg/kg/day. The relative concentrations of the metabolites and 18-MC were determined by the peak-heights by UPLC/MS/MS method. Major metabolites were identified as M5»M2»P2. Metabolite M4 was on the borderline to be considered a major metabolite. The parent 18-MC exposure was less than 3% of the total drug and metabolite exposure.

Generally the 18-MC exposure was independent of sex. The exposure increased less than proportional with the dose, being more noticeable between the middle and high dose groups. There was no accumulation of 18-MC when the parameters on the first and last day of dosing are compared and instead the exposure appeared to decrease with repeat dosing. The absorption appeared to be rapid with the $T_{max}$ at the time of the first plasma sample (1 hour) in most animals.

Plasma Protein Binding Studies

18-MC exhibited similar degree of protein binding, 92-98% on average, in all species tested (TABLE 4). There is no information on the protein binding of any of the metabolites.

TABLE 4

Protein Binding in Difference Species

| Species | Target Concentration (ng/mL) | % Bound Mean ± SD | Average % Bound Mean ± SD |
|---------|---|---|---|
| Mouse | 200 | 97.0 ± 0.208 | 96.9 ± 0.321 |
| | 600 | 97.1 ± 0.058 | |
| | 5,000 | 96.5 ± 0.071 | |
| Rat | 200 | 92.9 ± 0.351 | 92.7 ± 2.36 |
| | 600 | 94.9 ± 0.794 | |
| | 5,000 | 90.2 ± 0.153 | |
| Dog | 200 | 92.1 ± 1.78 | 93.4 ± 1.36 |
| | 600 | 94.8 ± 1.42 | |
| | 5,000 | 93.2 ± 0.153 | |
| Monkey | 200 | 98.4 ± 0.643 | 97.8 ± 0.603 |
| | 600 | 97.7 ± 0.100 | |
| | 5,000 | 97.2 ± 0.100 | |
| Human | 200 | 96.8 ± 0.321 | 96.5 ± 1.22 |
| | 600 | 97.6 ± 0.153 | |
| | 5,000 | 95.2 ± 0.473 | |

In Vitro Inhibition of Human Cytochrome P450 Isoenzymes by 18-MC HCl

The potential for 18-MC to inhibit metabolic isozymes was evaluated with recombinant human CYP enzymes 1A2, 2A6, 2B6, 2C8, 2C9, 2C19, 2D6, 2E1, and 3A4 (TABLE 5). Control incubations were performed for each assay with appropriate positive inhibitory controls. There is no data on the inhibitory potential of any of the metabolites on the isozymes.

TABLE 5

Summary of $IC_{50}$ values

| | $IC_{50}$ (μM) | |
|---|---|---|
| Isoform | 18-MC | Positive Control |
| CYP1A2 | NI | 4.2 |
| CYP2A6 | NI | 1.5 |
| CYP2B6 | >100 | 0.2 |
| CYP2C8 | 19 | 0.4 |
| CYP2C9 | 4.1 | 0.4 |
| CYP2C19 | 4.9 | 1.5 |
| CYP2D6 | >100 | 0.01 |
| CYP2E1 | 28 | 0.8 |
| CYP3A4-BFC | 13 | 0.01 |
| CYP3A4-DBF | NI | 0.002 |

NI = No inhibition detected

Example 5

Toxicology

14-Day Oral Gavage Toxicity in CD-1 Mice with a 14-Day Recovery Period

The potential toxicity and toxicokinetic profile of 18-MC HCl was investigated in a GLP study in which 18-MC HCl was administered daily by oral gavage to CD-1 mice for 14 consecutive days and evaluated the recovery, persistence, or progression of any effects following a minimum of a 14-day recovery period.

Study Methods

This study was designed to assess the toxicological effects of 18-MC HCl in CD-1 mice when dosed at 0, 25, 50, or 100 mg/kg/day for 14 days by oral gavage following a 2 to 4 day dose up-titration regimen, with expanded assessments of potential neurotoxicity and a 14 day recovery segment (TABLE 6).

TABLE 6

Study Design 2-Week Mouse Study

| Group Number | Treatment | Dosage Level (mg/kg/day) | Dose Volume (mL/kg) | Number of Animals[a,b,c] Males | Females |
|---|---|---|---|---|---|
| 1 | Vehicle Control | 0 | 10 | 25 | 25 |
| 2 | 18-MC HCl | 25 | 10 | 20 | 20 |
| 3 | 18-MC HCl | 50 | 10 | 20 | 20 |
| 4 | 18-MC HCl | 100 | 10 | 25 | 25 |

[a]Group 1, vehicle (5% dextrose, pH 3.0), was dosed for 18 consecutive days (study days −4 through 13), which corresponded to Group 4. Group 2 was dosed with 12.5 mg/kg/day (study days −2 and −1) and 25 mg/kg/day (study days 0 through 13). Group 3 was dosed with 12.5 mg/kg/day (study day − 3), 25 mg/kg/day (study day −2), 37.5 mg/kg/day (study day −1), 50 mg/kg/day (study days 0 through 13). Group 4 was dosed with 12.5 mg/kg/day (study day −4), 25 mg/kg/day (study day −3), 50 mg/kg/day (study day −2), 75 mg/kg/day (study day −1), and 100 mg/kg/day (study days 0 through 13).
[b]15 animals/sex/group were selected for the primary necropsy, with 10 animals/sex/group used for necropsy, clinical pathology, organ weight, and microscopic evaluation, and 5 animals/sex/group perfused for neuropathology assessment.
[c]The remaining 5 or 10 animals/sex/group were euthanized following a 14-day nondosing (recovery) period, with 5 animals/sex/group used for necropsy, clinical pathology, organ weight, and microscopic evaluation, and the remaining 5 animals/sex in the control and 100 mg/kg/day groups perfused for neuropathology assessment.

All test article-treated animals underwent up-titration of dosage levels prior to reaching the maximum daily dose, which was administered for 14 consecutive days. The up-titration was performed because earlier studies indicated that tolerability may have been improved by slowly ramping up the dose. The dose volume was 10 mL/kg for all groups. Groups 1 and 4 each consisted of 25 animals/sex and Groups 2-3 each consisted of 20 animals for each sex. Following 14 days of dose administration, 15 mice/sex/toxicology group were euthanized; the remaining 5, (10 for the control and high dose group) mice/sex/toxicology group were euthanized following a 14-day nondosing (recovery) period. Following the final blood collection (study day 13), all toxicokinetic animals (from a satellite group of 18 animals/sex/ dose level) were euthanized.

[a] Group 1, vehicle (5% dextrose, pH 3.0), was dosed for 18 consecutive days (study days −4 through 13), which corresponded to Group 4. Group 2 was dosed with 12.5 mg/kg/day (study days −2 and −1) and 25 mg/kg/day (study days 0 through 13). Group 3 was dosed with 12.5 mg/kg/day (study day −3), 25 mg/kg/day (study day −2), 37.5 mg/kg/day (study day −1), 50 mg/kg/day (study days 0 through 13). Group 4 was dosed with 12.5 mg/kg/day (study day −4), 25 mg/kg/day (study day −3), 50 mg/kg/day (study day −2), 75 mg/kg/day (study day −1), and 100 mg/kg/day (study days 0 through 13).

[b] 15 animals/sex/group were selected for the primary necropsy, with 10 animals/sex/group used for necropsy, clinical pathology, organ weight, and microscopic evaluation, and 5 animals/sex/group perfused for neuropathology assessment.

[c] The remaining 5 or 10 animals/sex/group were euthanized following a 14-day nondosing (recovery) period, with 5 animals/sex/group used for necropsy, clinical pathology, organ weight, and microscopic evaluation, and the remaining 5 animals/sex in the control and 100 mg/kg/day groups perfused for neuropathology assessment.

For toxicology assessment, all animals were observed twice daily for mortality and moribundity. Clinical observations were recorded daily, and detailed physical examinations were conducted weekly. Body weights and food consumption were recorded twice weekly. Body temperature was recorded prior to dosing and following dosing at the time that post-dosing clinical observations were conducted. Functional observational battery (FOB) data were recorded for all animals near the start of the treatment period, near the end of the treatment period, and near the end of the recovery period. Ophthalmic examinations were performed during pretest and near the end of the dosing period. At the primary necropsy 10 animals/sex/group and at the recovery necropsy 5 animals/sex/group, were selected for complete necropsies, clinical pathology assessment (hematology and serum chemistry), organ weight collection, and microscopic examination of a full list of tissues. At each termination interval, 5 animals/sex/group were assigned for neuropathology assessments that involved perfusion fixation, comprehensive sectioning of the brain and collection of selected peripheral nerves, and the employment of special stains used to detect subtle neuronal injury.

Toxicology Results

One male assigned to the 100 mg/kg/day group was found dead on study day −1 during the up-titration period, following 4 doses (12.5, 25, 50, and 75 mg/kg/day) and exhibited no significant clinical signs. Another male was found dead on study day 12, with clinical findings of clonic convulsions, hypoactivity, splayed hindlimbs, and decreased respiration. The death of the male that exhibited the clinical signs was considered test article related, whereas the relationship of test article to the other male's death was less certain. There were no microscopic, macroscopic, or clinical observation findings that definitively determined a cause of death of either animal. Specifically, the causes of death for these males were undetermined microscopically although both had atrial and/or left ventricular dilatation noted in the heart. These findings were not observed in any animals that survived to the scheduled necropsies and as such are not clearly directly related to test article administration.

Two females were found dead (one control and one treated with 50 mg/kg/day on study days 4 and 2, respectively). Both deaths were unrelated to test article; the death of the 50 mg/kg/day female was attributable to trauma.

All other main study animals survived to the scheduled necropsies.

In addition to the findings in the one 100 mg/kg/day male that died on Day 12, test article-related clinical observations were noted at approximately 1 hour following dose administration during the dosing period and included soft stool for males in the 50 mg/kg/day group and males and females in the 100 mg/kg/day group. In addition, findings of a cool body, brown material around the anogenital area, and diarrhea were noted sparingly for males in the 100 mg/kg/day group.

There was no test article related findings in: body weights; food consumption; home cage, handling, open field, sensory, or neuromuscular observations; or organ weights. There were no toxicologically significant test article-related alterations in hematology, bone marrow cytology, serum chemistry, or ophthalmic examinations. There were no test article-related changes in the neuropathology gross necropsy, brain weights or measurements, or microscopic evaluation.

There were physiological changes in body temperature. Mean body temperatures for males and females in the 100 mg/kg/day group were lower than the control group at 1 hour post-dosing on study day 0; the difference in males was significant ($p<0.05$). At 1 hour post-dosing on study day 13, significantly ($p<0.01$ or $p<0.05$) lower body temperature was noted for males in the 50 and 100 mg/kg/day groups and females in the 100 mg/kg/day group. These findings were considered test article related but non-adverse and corresponded to clinical findings of cool body.

Toxicokinetic Results

Toxicokinetic parameters are presented in TABLE 7.

TABLE 7

Summary of Toxicokinetic Parameters of 18-MC HCl

| | | Sex | | | | | |
|---|---|---|---|---|---|---|---|
| | | Male | | | Female | | |
| | | 18-MC HCl Dose (mg/kg/day) | | | | | |
| Day | | 25 | 50 | 100 | 25 | 50 | 100 |
| 0 | $C_{max}$, ng/mL | 19.4 | 44.3 | 131 | 30.8 | 23.7 | 51.8 |
| | $T_{max}$, h | 0.500 | 0.500 | 1.00 | 0.500 | 0.500 | 1.00 |
| | $T_{1/2}$, h | NC | NC | NC | NC | NC | NC |
| | $AUC_{(0-24)}$, ng · h/mL | 66.6 | 108 | 349 | 77.8 | 56.2 | 187 |
| | $C_{max}$ Ratio (Male/Female) | 0.630 | 1.87 | 2.53 | — | — | — |
| | $AUC_{(0-24)}$ Ratio (Male/Female) | 0.856 | 1.92 | 1.87 | — | — | — |
| 13 | $C_{max}$, ng/mL | 23.6 | 92.9 | 136 | 25.6 | 49.9 | 44.0 |
| | $T_{max}$, h | 0.500 | 0.500 | 0.500 | 0.500 | 0.500 | 0.500 |
| | $T_{1/2}$, h | NC | 1.78 | 1.93 | NC | NC | 2.45 |
| | $AUC_{(0-24)}$, ng · h/mL | 50.5 | 164 | 329 | 54.5 | 119 | 188 |
| | $C_{max}$ Ratio (Male/Female) | 0.922 | 1.86 | 3.09 | — | — | — |
| | $AUC_{(0-24)}$ Ratio (Male/Female) | 0.927 | 1.38 | 1.75 | — | — | — |
| | $C_{max}$ Ratio (Day 13/Day 0) | 1.22 | 2.10 | 1.04 | 0.831 | 2.11 | 0.849 |
| | $AUC_{(0-24)}$ Ratio (Day 13/Day 0) | 0.758 | 1.52 | 0.943 | 0.701 | 2.12 | 1.01 |

In general, 18-MC exposure ($C_{max}$ and $AUC_{(0-24)}$) increased with dose in both sexes for the single and repeated doses. The exposure in males was higher than females on both study days. There was no apparent accumulation of 18-MC in mice following repeated daily dosing for 14 days, which is consistent with the short half-life of 18-MC.

18-MC HCl was administered orally by gavage once daily for 14 consecutive days to 3 toxicological groups (Groups 2-4) and 3 toxicokinetic groups (Groups 2A-4A) of Crl:CD1 (ICR) mice. Mortality was noted for one male in the 100 mg/kg/day group during the treatment phase. A cause of death of this animal was not determined microscopically but exaggerated pharmacological effects of the test article (clonic convulsions, hypoactivity, splayed hindlimbs, and decreased respiration) were noted prior to death. Therefore, a dosage level of 50 mg/kg/day was considered as the no-observed-adverse-affect level (NOAEL) for males and 100 mg/kg/day for females, corresponding to $AUC_{(0-24)}$ values of 164 ng×h/mL and 188 ng×h/mL, respectively, on study day 13. With the exception of a non-adverse decreased body temperature in males and females at 50 and 100 mg/kg/day, there were no noted neurobehavioral findings as measured in the Functional Observational Battery.

14-Day Oral Gavage Toxicity and Toxicokinetics in Monkeys with a 4-Week Recovery Period The toxicokinetics and toxicity profile of 18-MC HCl was investigated in a GLP study in which 18-MC HCl was administered daily for 14 consecutive days to cynomolgus monkeys.

Young adult male and female cynomolgus monkeys were administered 18-MC HCl by nasogastric gavage for 14 consecutive days at doses of 0 (vehicle=5% dextrose, pH=3), 50, 150, or 400/300 mg/kg/day. Due to severe clinical observations seen on the first day of dosing in the high dose group, the dose was subsequently reduced from 400 to 300 mg/kg/day. The study design is summarized in TABLE 8 below.

TABLE 8

Study Design of the 2-Week Monkey Study

| Group No. | Dose Level (mg/kg/day) | Dose Volume (mL/kg) | Dose Concentration (mg/mL) | No. of Animals Primary necropsy | | No. of Animals Recovery necropsy | |
|---|---|---|---|---|---|---|---|
| | | | | Male | Female | Male | Female |
| 1 | 0 | 10 | 0 | 3 | 3 | 2 | 2 |
| 2 | 50 | 10 | 5 | 3 | 3 | 2 | 2 |
| 3 | 150 | 10 | 15 | 3 | 3 | 2 | 2 |
| 4[a] | 400/300 | 7.5/10 | 40/30 | 3 | 3 | 2 | 2 |

[a]Beginning on Day 2 (second day of dosing), the dose volume was decreased from 10 mL/kg to 7.5 mL/kg in order to reduce the dose level of the high dose group to 300 mg/kg/day due the severity of clinical observations seen on Day 1. On Day 8, the dose volume was raised to 10 mL/kg and the dose concentration lowered to 30 mg/mL.

Assessments of neurobehavioral effects and general toxicity were based on mortality, functional observational battery (FOB) evaluations, clinical observations, body weight, and body temperature; ophthalmoscopic, electrocardiographic examinations; and anatomic and clinical pathology. The anatomical pathology evaluations included histopathology of a full list of tissues from all animals and a comprehensive evaluation of the central nervous system (including selected peripheral nerves) utilizing whole body perfusion and special stains. Bone marrow smears from all animals were evaluated microscopically. Complete differentials and myeloid-erythroid (ME) ratios were performed. Toxicokinetic assessment was conducted for the test article and metabolites.

[a] Beginning on Day 2 (second day of dosing), the dose volume was decreased from 10 mL/kg to 7.5 mL/kg in order to reduce the dose level of the high dose group to 300 mg/kg/day due the severity of clinical observations seen on Day 1. On Day 8, the dose volume was raised to 10 mL/kg and the dose concentration lowered to 30 mg/mL.

There were no 18-MC-related ophthalmoscopic observation findings, alterations among urinalysis or, coagulation parameters in either sex at any dose level. No 18-MC-related findings among bone marrow parameters were observed in females at any dose. Findings in the neurological examinations were consistent with those reported as part of the clinical observations. No MC-18-related microscopic findings were observed in the brain, spinal cord, phrenic nerves, or vagus nerves using hematoxylin and eosin, luxol fast blue, and fluro jade staining techniques.

There were no electrocardiographic changes that were directly attributable to administration of 18-MC HCl. One animal that died on Day 1 (see below) exhibited marked first degree AV block, an interventricular conduction disturbance and sinus bradycardia on the Day 1 post dose ECG. On Day 1, another high-dose animal that was sedated at the time of measurement had a wide complex tachycardia that was probably junctional tachycardia with aberrancy. The effects were likely indirect effects related to the marked clinical signs seen in this animal at the time of measurement. No electrocardiographic effects were seen in 18-MC HCl treated animals at the end of the treatment period. Consistent with the absence of electrocardiographic observations in all but the two animals mentioned above following treatment with 400 mg/kg. No cardiovascular findings were reported in the cardiovascular safety pharmacology study, in which telemetered monkeys were given doses as high as 270 mg/kg.

One male treated with 400 mg/kg died in extremis immediately prior to a planned euthanasia in extremis due to 18-MC-related effects noted following dosing on Day 1. There were no 18-MC-related macroscopic or microscopic observations noted, however, and a cause of death for this animal could not be determined. Based on this death, the dose level for this group was subsequently decreased to 300 mg/kg/day (effective on Day 2) for the remainder of the dosing period.

18-MC-related clinical signs noted at 400 mg/kg/day (Day 1) included eye lid(s) partially or completely closed, decreased activity, hunched posture, and salivation all with a low number of animals affected and low incidence. At 300 mg/kg/day, 18-MC-related clinical signs of decreased activity, ataxia, inappetence, salivation, hunched posture, emesis, vomitus, and eyelid partially/completely closed were noted, all at low incidence. At 150 mg/kg/day, a few occurrences of decreased activity, inappetence, eyelid partially/completely closed were noted in a small number of animals.

Additional signs noted occasionally at doses 50 mg/kg/day that were related to the administration of 18-MC were watery and/or soft feces, vomitus and/or emesis.

Mean body weight/body weight gain was slightly reduced in animals receiving 18-MC HCl. In this regard, mean cumulative body gain (Days 1-14) in males/females were −0.042/+0.04 kg, −0.22/−0.08 kg, −0.28/−0.12 kg and −0.23/−0.09 kg, respectively.

Hematological changes consisted of 18-MC-related mild to moderate decreases in red cell mass in both sexes at doses 50 mg/kg/day that were associated with occasional reductions in reticulocytes. There were no meaningful effects on erythrocyte morphology. Mild decreases in total leukocytes (attributable to lymphoid and myeloid cells) were noted in males at 400/300 mg/kg/day and in females at all dose levels. TABLE 9 summarizes these hematological changes.

TABLE 9

Summary of Effects on Hematology Parameters[a]

| Parameter | 50 mg/kg/day | | 150 mg/kg/day | | 400/300 mg/kg/day | |
|---|---|---|---|---|---|---|
| | M | F | M | F | M | F |
| Hemoglobin | NC | NC | −17% | −19% | −20% | −17% |
| Leukocytes | NC | −29% | NC | −33% | −40% | −45% |
| Neutrophils | NC | −29% | NC | −36% | −20% | −47% |
| Lymphocytes | NC | −26% | NC | −28% | −45% | −41% |
| Monocytes | NC | NC | NC | −81% | −84% | −77% |

[a]Change relative to pretest mean;
+: increase;
−: decrease
M = males;
F = females;
NC: no toxicologically relevant change

[a]Change relative to pretest mean; +: increase; −: decrease
M=males; F=females; NC: no toxicologically relevant change Clinical chemistry changes were limited to mild decreases in alkaline phosphatase and total bilirubin in both sexes at all dose levels and mild decreases in phosphorus in females at doses 150 mg/kg/day and sodium and chloride in males at doses 150 mg/kg/day (TABLE 10). These changes were not considered to be of significant toxicological relevance.

18-MC-related macroscopic observations at terminal necropsy were limited to the thymus. Mildly small thymus was observed at 50 mg/kg/day and at 400/300 mg/kg/day. The mildly small thymus correlated microscopically with test article-related generalized lymphoid depletion.

Organ weight findings at terminal necropsy were observed in the liver (increase) and thymus (decrease) at doses 50 mg/kg/day. These organ weight differences were associated with microscopic findings in the respective organs. The following table summarizes the differences in mean organ weight values between control and 18-MC HCl treated animals.

TABLE 10

Test Article-related Organ Weight Changes - Terminal Male and Female

| | Percent Change Relative to Control Dose level | | | | | |
|---|---|---|---|---|---|---|
| | 50 mg/kg/day | | 150 mg/kg/day | | 400/300 mg/kg/day | |
| | Sex | | | | | |
| | M | F | M | F | M | F |
| | Number Examined | | | | | |
| | 3 | 3 | 3 | 3 | 3 | 3 |
| Liver (g) | ↑26.36 | ↑52.66$^a$ | ↑48.43$^a$ | ↑43.49$^a$ | ↑65.98$^a$ | ↑50.04$^a$ |
| Liver/BWt % | ↑22.10 | ↑51.23$^b$ | ↑55.92$^b$ | ↑55.09$^b$ | ↑69.67$^b$ | ↑67.01$^b$ |
| Liver/BrWt ratio | ↑22.11 | ↑47.26$^a$ | ↑55.79$^a$ | ↑42.30$^a$ | ↑46.39 | ↑58.79$^b$ |
| Thymus (g) | ↓35.06 | ↓35.14 | ↓47.41 | ↓52.77 | ↓78.63$^a$ | ↓79.51$^a$ |
| Thymus/BWt % | ↓36.35 | ↓32.52 | ↓43.99 | ↓49.41 | ↓77.39$^a$ | ↓77.62 |
| Thymus/BrWt ratio | ↓34.90 | ↓37.01 | ↓45.30 | ↓52.39 | ↓81.19$^a$ | ↓78.17$^a$ |

$^a$Significantly different from control; (p < 0.05)
$^b$Significantly different from control; (p < 0.01)
BWt—Body Weight
BrWt—Brain Weight
↑—Increased
↓—Decreased
M—Male
F—Female 18-MC-related microscopic findings were observed in the liver and thymus of male and female terminal animals at ≥50 mg/kg/day and the bone marrow (femur, rib, and sternum) of terminal males at ≥150 mg/kg/day and females at ≥400/300 mg/kg/day.

In the thymus, lymphoid depletion in the cortex or throughout the tissue was noted. Though thymic lymphoid depletion is often considered a secondary/stress-related change, the severity of the thymic lymphoid depletion noted in females administered doses ≥50 mg/kg/day was considered adverse. The incidence and severity of the microscopic thymic changes are summarized in TABLE 11 below.

TABLE 11

Test Article-related Microscopic Observations Thymus - Terminal

| | Number with Observation Dose level (mg/kg/day) | | | | | | | |
|---|---|---|---|---|---|---|---|---|
| | 0 | | 50 | | 150 | | 400/300 | |
| | Sex | | | | | | | |
| | M | F | M | F | M | F | M | F |
| | Number Examined | | | | | | | |
| Thymus | 3 | 3 | 3 | 3 | 3 | 3 | 4 | 3 |
| Depletion, lymphoid, cortex | 0 | 0 | 2 | 2 | 3 | 3 | 0 | 0 |
| minimal | 0 | 0 | 2 | 2 | 1 | 0 | 0 | 0 |
| mild | 0 | 0 | 0 | 0 | 2 | 2 | 0 | 0 |
| moderate | 0 | 0 | 0 | 0 | 0 | 1 | 0 | 0 |
| Depletion lymphoid, generalized | 0 | 0 | 0 | 1 | 0 | 0 | 3 | 3 |
| mild | 0 | 0 | 0 | 1 | 0 | 0 | 1 | 2 |
| moderate | 0 | 0 | 0 | 0 | 0 | 0 | 2 | 1 |

In the liver, the hepatocellular hypertrophy associated with the liver weight increases noted was considered an adaptive response and non-adverse (TABLE 12).

TABLE 12

Test Article-related Microscopic Observations Liver - Terminal

| | Number with Observation Dose level: mg/kg/day | | | | | | | |
|---|---|---|---|---|---|---|---|---|
| | 0 | | 50 | | 150 | | 400/300 | |
| | Sex | | | | | | | |
| | M | F | M | F | M | F | M | F |
| | Number Examined | | | | | | | |
| Liver | 3 | 3 | 3 | 3 | 3 | 3 | 4 | 3 |
| Hypertrophy, hepatocellular, panlobular | 0 | 0 | 0 | 3 | 3 | 3 | 3 | 3 |
| minimal | 0 | 0 | 0 | 0 | 0 | 1 | 0 | 0 |
| mild | 0 | 0 | 0 | 3 | 3 | 2 | 3 | 3 |

Bone marrow depletion noted in males at doses 150 mg/kg/day and in high-dose animals was considered adverse. The incidence and severity of this microscopic observation is summarized in TABLE 13 below.

TABLE 13

Test Article-related Microscopic Observations Bone Marrow - Terminal

| | Number with Observation Dose level: mg/kg/day | | | | | | | |
|---|---|---|---|---|---|---|---|---|
| | 0 | | 50 | | 150 | | 400/300 | |
| | Sex | | | | | | | |
| | M | F | M | F | M | F | M | F |
| | Number Examined | | | | | | | |
| | 3 | 3 | 3 | 3 | 3 | 3 | 4 | 3 |
| Bone marrow, femur | | | | | | | | |
| Depletion, mixed | 0 | 0 | 0 | 0 | 1 | 0 | 2 | 1 |
| minimal | 0 | 0 | 0 | 0 | 1 | 0 | 0 | 1 |
| mild | 0 | 0 | 0 | 0 | 0 | 0 | 1 | 0 |
| moderate | 0 | 0 | 0 | 0 | 0 | 0 | 1 | 0 |
| Bone marrow, rib | | | | | | | | |
| Depletion, mixed | 0 | 0 | 0 | 0 | 1 | 0 | 2 | 1 |
| minimal | 0 | 0 | 0 | 0 | 1 | 0 | 0 | 0 |

TABLE 13-continued

Test Article-related Microscopic Observations
Bone Marrow - Terminal

Number with Observation
Dose level: mg/kg/day

| | 0 | | 50 | | 150 | | 400/300 | |
|---|---|---|---|---|---|---|---|---|
| | \multicolumn{8}{c}{Sex} |
| | M | F | M | F | M | F | M | F |
| | \multicolumn{8}{c}{Number Examined} |
| | 3 | 3 | 3 | 3 | 3 | 3 | 4 | 3 |
| mild | 0 | 0 | 0 | 0 | 0 | 0 | 1 | 1 |
| moderate | 0 | 0 | 0 | 0 | 0 | 0 | 1 | 0 |
| Bone marrow, sternum | | | | | | | | |
| Depletion, mixed | 0 | 0 | 0 | 0 | 1 | 0 | 2 | 1 |
| minimal | 0 | 0 | 0 | 0 | 1 | 0 | 0 | 0 |
| mild | 0 | 0 | 0 | 0 | 0 | 0 | 1 | 1 |
| moderate | 0 | 0 | 0 | 0 | 0 | 0 | 1 | 0 |

Given the bone marrow findings summarized above, complete differentials and myeloid/erythroid (M/E) ratios were performed. In males receiving 400/300 mg/kg/day, a mild increase in the M/E ratio (+59%) relative to controls was observed. These findings were generally attributable to reductions in erythroid cells in the two animals which had available data at this dose level. One 400/300 mg/kg/day male had reduced reticulocytes which is consistent with increased M/E ratio. Another 400/300 mg/kg/day male had a mildly increased M/E ratio without an apparent reduction in reticulocytes. The reason for the disharmony between the hematology data and the bone marrow findings is uncertain but may be a reflection of manual hematology differentials (less accurate relative to automated). All of these findings were considered 18-MC-related and reflect altered and/or reduced hematopoietic cell populations in the bone marrow.

Systemic exposure to 18-MC was independent of sex. Individual 18-MC plasma concentration-time profiles, Cmax, and AUC values were variable and displayed no consistent differences between males and females on Day 1 and Day 14 (the sex ratios ranged from 0.502 to 1.70). The following discussion is therefore based on data for males and females combined.

The variability in mean 18-MC plasma concentrations, as measured by CV %, were similar across dose groups and ranged from 38% to 110% on Day 1 and 36% to 154% on Day 14. Median 18-MC plasma concentrations were quantifiable up to 24 hours post dose for all dose groups on Days 1 and 14 (individual Tlast values ranged from 12 to 24 hours post dose). Median peak 18-MC plasma concentrations were observed by 1 hour post dose for all dose groups on Days 1 and 14 (individual Tmax values ranged from 0 to 12 hours post dose).

Following oral gavage administration of 18-MC HCl, Cmax and mean systemic exposure (AUC0-24) values of 18-MC increased with increasing dose. A 1:3:8-fold increase in dose resulted in an approximate 1:1.4:2.3-fold increase in Cmax and an approximate 1:2.6:3.9-fold increase in AUC0-24 on Day 1. On Day 14, a 1:3:6-fold increase in dose resulted in an approximate 1:1.3:2.2-fold increase in Cmax and an approximate 1:2.1:3.6-fold increase in AUC0-24.

Systemic exposure (AUC0-24) generally appeared to decrease following repeated administration of 18-MC HCl. Accumulation ratios could not be determined for the high dose group due the change in dose from 400 to 300 mg/kg following the Day 1 administration. Individual accumulation ratios ranged from 0.297 to 0.866 for the 50 mg/kg dose group with the exception of two females with R values of 1.12 and 2.94, respectively, and ranged from 0.254 to 0.939 for the 150 mg/kg dose group.

Mean accumulation ratios were 0.912 and 0.596 for the 50 and 150 mg/kg dose groups, respectively.

In conclusion:

Systemic exposure to 18-MC was independent of sex. Individual 18-MC plasma concentration-time profiles, Cmax, and AUC values were variable and displayed no consistent differences between males and females on Day 1 and Day 14.

Following oral gavage administration of 18-MC HCl, mean systemic exposure (AUC0-24) values of 18-MC increased with increasing dose in an approximate dose proportional manner from the low to mid-dose group on Day 1, and in a less than dose proportional manner across the dose range on Days 1 and 14.

Following oral gavage administration of 18-MC HCl, mean systemic exposure Cmax values of 18-MC increased with increasing dose in a less than dose proportional manner across the dose range on Days 1 and 14.

Systemic exposure (AUC0-24) generally appeared to decrease following repeated administration.

Following 14 days of oral 18-MC administration to male and female monkeys (and in the absence of forthcoming recovery/reversibility data), the NOAEL was 50 mg/kg/day, the low dose level of the study. On Day 14, 18-MC plasma $AUC_{0-24}$ and $C_{max}$ values at 400 mg/kg for 1 day followed by 300 mg/kg/day (the NOAEL dose) for t 13 days were 144 μg×hr/mL and 1210 μg/mL, respectively, averaged across the sexes.

Genetic Toxicity

Four GLP studies were performed to assess the genotoxic potential of 18-MC HCl. These tests consisted of two in vitro tests including bacterial mutagenicity (Ames test) and mammalian clastogenicity (chromosome aberration in cells) studies. Two in vivo GLP studies were also conducted. A GLP in vivo micronucleus test with mouse bone marrow and a GLP comet assay study evaluating genetic damage in the liver of mice following oral dosing using single cell gel electrophoresis. In each assay, 18-MC HCl was tested in the absence and presence of metabolic activation (Aroclor-induced rat liver S-9). All in vivo assays employed maximum tolerated doses. Preliminary screening Ames and in vivo micronucleus assays were also conducted and the results consistent with those reported in the definitive studies.

Bacterial Reverse Mutation Assay

A preliminary non-GLP study evaluated the in vitro mutagenicity of 18-MC HCl in the Ames test. The tester strains used were *Salmonella typhimurium* histidine auxotrophs TA98, TA100, TA1535, and TA1537 and *Escherichia coli* WP2 uvrA. The test article was tested at concentrations of up to 5000 μg/plate, along with appropriate vehicle control and positive controls. 18-MC HCl did not cause mutagenic response in any of the tester strains in either the absence or the presence of Aroclor-induced rat liver S9. The test article precipitated at the top 2 concentrations In the GLP study, 18-MC HCl was further evaluated for mutagenic activity in the in vitro *Salmonella-E. coli*/mammalian microsome reverse mutation assay using the plate incorporation method. Four tester strains of *Salmonella typhimurium* (TA1537, TA98, TA100, and TA1535) and one *Escherichia coli* strain (WP2 uvrA) were used. 18-MC HCl was prepared as a formulation in dimethylsulfoxide (DMSO) and tested at concentrations of up to 500 μg/plate.

Mutagenicity testing was performed in triplicate at each concentration with and without an AROCLOR™ 1254-induced rat liver S9 metabolic activation system.

Criteria for a negative response were met for all tester strains, with and without metabolic activation. Mean number of revertant colonies following incubation with 18-MC HCl was comparable to historical control ranges at all concentrations for all tester strains with and without metabolic activation. The data from the vehicle and positive controls demonstrated the validity and sensitivity of this test system for detecting chemical mutagens with and without metabolic activation.

These data support the conclusion that 18-MC HCl is negative for mutagenic activity in the *Salmonella* strains TA1537, TA98, TA100, and TA1535 and in the *E. coli* strain WP2 uvrA, with and without metabolic activation.

In Vitro Chromosome Aberration Test in Cultured Human Peripheral Blood Lymphocytes In a GLP study, 18-MC HCl was evaluated for the potential to induce chromosome aberrations in human peripheral blood lymphocytes (HPBL) during short (3-hour) and long (22-hour) incubations with or without an exogenous metabolic activation system.

18-MC HCl was formulated in DMSO and tested in the range-finding assay up to approximately 1 mM, the highest concentration recommended per current regulatory guidance. HPBL cultures were treated with the test article, positive control or vehicle control in the presence and absence of an Aroclor™ 1254-induced rat liver S9 microsomal fraction. Precipitates were observed at the end of treatment at ≥46.3 µg/mL (0.11 mM) in the 22-hour treatment without metabolic activation and at ≥92.5 µg/mL (0.22 mM) in the 3-hour treatments with and without metabolic activation. Based on precipitates observed in the range-finding assay, concentrations used during the definitive chromosome aberration assay were a) 7.5, 15, 25, 50, 100, and 150 µg/mL in the 3-hour treatments with and without metabolic activation, and b) 1.0, 15, 25, 30, 35, 40, 45, 50, 55, 60, and 75 µg/mL in the 22-hour treatment without metabolic activation. These cultures along with the vehicle and one concentration of positive control for each treatment condition were analyzed for aberrations. Structural chromosome aberrations were scored for each concentration from a total of 200 metaphase cells (when possible) or 30 aberrant cells. Numerical aberrations were evaluated in 400 metaphase cells per concentration.

A statistically significant increase (p≤0.01) in the percent of cells with structural chromosome aberrations was observed in the 3-hour treatment with metabolic activation at 50 and 100 µg/mL (or 123 and 247 µM). Additionally, a statistically significant increase (p≤0.01) in the percent of cells with greater than one aberration was observed in the 3-hour treatment with metabolic activation at 100 µg/mL (246 µM). No statistically significant differences in the percent of cells with structural chromosome aberrations or the percent of cells with greater than one aberration were noted in either the 3- or 22-hour treatments without metabolic activation. There was no statistically significant test article-related increase in numerical aberrations (polyploidy or endoreduplication) in any treatment compared to the vehicle controls. The aberrations in vehicle and positive control cultures were comparable to acceptable historical control ranges.

Based upon the results of this assay, 18-MC HCl was considered positive for inducting structural aberrations in HPBL with metabolic activation and negative for inducing structural aberrations in HPBL without metabolic activation under the conditions of this test system. These in vitro results were not corroborated in mice following oral administration. No evidence of clastogenicity or genotoxicity was observed in the in vivo micronucleus assay or the in vivo comet test.

Mouse Bone Marrow In Vivo Micronucleus Assay

The potential of 18-MC to induce micronuclei in polychromatic erythrocytes in mouse bone marrow in order to assess its potential in vivo clastogenic activity and/or to disrupt the mitotic apparatus.

Initially, a non-GLP screening study evaluated the toxicity and genotoxicity of 18-MC in ICR mice following a single oral administration of 18-MC HCl at dose levels of 100, 150, 200, 250, 300 and 400 mg/kg formulated in phosphate buffered saline, pH 7.4, as a suspension (not the formulation utilized for GLP studies). Treatment resulted and clinical signs of lethargy and piloerection at doses of 200-400 mg/kg and in mortality of male and female ICR mice at doses of 300 and 400 mg/kg. The highest non-lethal dose was 250 mg/kg. No significant increase in the incidence of micronucleated polychromatic erythrocytes (MPCE) in bone marrow of male and female ICR mice at dose levels without mortality (250 mg/kg and less) was observed compared to vehicle control groups.

In the definitive GLP study, 18-MC HCl was formulated in the vehicle (5% dextrose, pH=3) and administered orally by gavage once daily for 3 consecutive days to male Crl:CD1(ICR) mice at dosage levels of 50, 75, and 120 mg/kg/day. These doses were based upon prior toxicology data indicating higher doses were associated with mortality in this species. A concurrent vehicle control group received the vehicle on a comparable regimen. A positive control group received a single oral dose of 60 mg/kg cyclophosphamide on Day 2, the day prior to the scheduled euthanasia. Each group consisted of 6 males. Males only were used as no significant differences in response related to gender were expected based upon prior toxicology and toxicokinetic data. All animals were euthanized on Day 3, the day following the final dose and discarded following bone marrow collection.

All animals were observed twice daily for mortality and moribundity. Bone marrow collection for micronucleus evaluation was performed for 5 of the 6 animals in each group at the scheduled euthanasia (Day 3). All animals were discarded without necropsy. Bone marrow smears were prepared, and the coded slides were counted for polychromatic, normochromatic, and micronucleated polychromatic erythrocytes following the final bone marrow sample collection on Day 3.

Lethality was observed in a single animal in the 120 mg/kg/day group within 3 hours of dosing. There were no remarkable clinical or macroscopic findings noted in this animal at necropsy. Given that a low frequency in mortality within 3 hours of dosing had been seen at this dose in prior studies, the death was considered test article-related. All other animals survived until the scheduled euthanasia.

There were no test article-related effects on clinical observations, body weights, or food consumption.

The test article did not produce an increase in the percent mean number of micronucleated polychromatic erythrocytes (% MN-PCEs) compared to the vehicle control. No bone marrow cytotoxicity (decreases in the ratio of polychromatic to total erythrocytes, PCE:TE ratio) was noted in any test article-treated group. Vehicle and positive control values were within the expected historic ranges validating the study results. Therefore, 18-MC met the criteria for a negative response for bone marrow cytotoxicity and clastogenic activity and/or disruption of the mitotic apparatus under the conditions of this assay.

In Vivo Comet Assay

The genotoxic potential of 18-MC HCl was evaluated for its ability to induce DNA damage in mouse liver using the principles of comet assay. The comet assay (alkaline single cell gel electrophoresis) is a microgel electrophoretic technique that detects DNA damage in individual cells. DNA damage can be expressed as DNA single strand breaks, double strand breaks, and strand breaks induced by alkali labile sites. This study was initiated on the basis of results of the in vitro chromosomal aberration assay that indicated a positive response with 18-MC HCl in the presence of metabolic activation. For this study, the liver was selected as the tissue for evaluation, since this tissue is expected to contain high concentrations of parent drug and metabolites following oral administration.

Male mice were administered oral doses of 0 (vehicle=5% dextrose), 50, 90 and 120 mg/kg/day by gavage according to the table below. Animals in groups 1-4 were dosed on three consecutive days and euthanized 3 to 4 hours after the last dose by $CO_2$ inhalation. A separate group of animals were dosed with methyl methanesulfonate (MMS) which served as a positive control. Immediately following euthanasia, the liver was removed and collected from each animal.

In this study, comet tail migration, % tail DNA (also known as % tail intensity) and tail moment were determined for each animal/treatment group and served as parameters of DNA damage. Though a statistically significant increase mean % tail DNA relative to the vehicle control was observed at a dose of 90 mg/kg/day (2.60+/−0.7 vs. 1.27+/−0.52), a similar increase was not seen in the high-dose group and the 90 mg/kg group mean value was well within the upper bound of the historical control range (mean−4.42). The positive control (MMS) produced the expected increases in comet parameters validating the results of the assay.

Based upon the results of this study, 18-MC HCl is considered negative in the mouse comet assay. These results are consistent with prior in vivo micronucleus studies and collectively suggest 18-MC HCl does not pose significant genotoxic risk.

Example 6

Clinical Study

Fourteen normal, healthy volunteers were enrolled in the study. Seven volunteers were treated in the first cohort (3 placebo, 4 received a single dose of 20 mg of 18-MC) and seven in the second cohort (2 placebo, 5 received 8 mg as 4 mg doses of 18-MC administered at 0 and plus 10 hours). For Cohort A, volunteers were monitored in a hospital unit for 2 days (36 hours) days, and were followed up for safety at Days 3, 7 and 30. For Cohort B, volunteers were monitored in a hospital unit for 2 days (36 hours), and were followed up for safety at Days 3, 4, 7 and 30.

Study objectives: To determine the safety and tolerability of the drug 18-MC, and to evaluate the biochemical (safety) parameters of the individual participants and to determine pharmacokinetic (PK) parameters.

Study Design

This study was designed as a randomized, double-blind, placebo-controlled, single-center Phase 1 first-in-human clinical trial. After screening, volunteers were admitted to the hospital for 36 hours. On the first day of dosing, a sentinel group of one active and one placebo were treated to evaluate any significant safety signal, the remaining volunteers were enrolled after the successful sentinel group. Study article was initiated on Day 1 and volunteers were discharged on Day 2. Cohort A were seen as outpatients on Days 3, 7 and 30. Cohort B were seen as outpatients on Days 3, 4, 7 and 30. 14 subjects were in the study, 5 male and 9 female. None discontinued the study.

The study plan as stated in the protocol was to include two cohorts treated as single dose treatment groups, the first to receive 20 mg of 18-MC or placebo (4 and 3 volunteers, respectively) and the second to receive 60 mg 18-MC or placebo (also 4 and 3, respectively). This was to be followed by a multi-dose protocol part with two cohorts. The subjects were to be administered three daily doses of 20 mg (5 active and 3 placebo) followed by another cohort with the subjects receiving 60 mg 18-MC (also 5 active and 3 placebo). An expansion of the multi-dose part was also planned, but neither the second single dose cohort nor the multi-dose treatment groups were conducted due to unexpectedly high plasma levels in the single dose treatment group.

The 20 mg treatment group of stage 1A returned plasma concentrations more than 20-fold higher than had been anticipated based upon nonclinical study results. As a result, an amendment (#2) to the protocol was filed and, instead of the planned 60 mg treatment group, seven volunteers were enrolled in a lower dose treatment group of 8 mg 18-MC or placebo (5 active and 2 placebo volunteers, respectively) administered as 4 mg in the morning and repeated 10 hours later was enrolled. TABLE 14 shows the dosage/formulation numbers:

TABLE 14

| Product Name and Potency | Dosage Form | Formulation No./Lot No. |
| --- | --- | --- |
| 18-MC | Drug API in 5% dextrose/Normal Saline | C001 (Cohort A) 9 Oct. 2014 (Cohort B) |
| Placebo | 5% dextrose/Normal Saline | C002 (Cohort A) 9 Oct. 2014 (Cohort B) |

Major inclusion criteria include: Men and/or non-pregnant women 18 years to a maximum of 40 years of age; subjects must be able to read, understand and sign the Statement of Consent; subjects must not be a carrier of any chronic disease that requires continuous use of any drug; and subjects must be in good physical and mental health, based on medical history, physical examination and laboratory results assessed during the selection process of volunteers.

Major exclusion criteria include: Abnormal biochemical parameters of blood and urine; history of major organ dysfunction, including but not limited to liver disease, heart disease, kidney disease; history of hypertension or hypertension; cancer or history of cancer; presence of any psychological abnormality at the discretion of the investigators, might interfere with the study; diabetes; any clinically important infectious disease, including but not limited to AIDS and hepatitis; substance abuse of tobacco or any other type of drug that can act in the CNS; and pregnancy.

Evaluation Criteria

All volunteers must sign the Statement of Informed Consent before any study procedures, including screening tests, are performed.

Determination of medical history is performed, including the evaluation of all inclusion and exclusion criteria, demographic data (age, sex, race, menstrual status, weight, height), history of present illness, history of hypersensitivity (allergy medications), history and general medical evaluation of all data including the current severity of symptoms.

A review of medication was performed, detailed physical examination was performed, adverse events were evaluated and graded.

Clinical laboratory: Hematology was performed: complete blood count (CBC), differential, platelet count, PT, PTT Serum chemistry: albumin, total protein, bilirubin, lactate dehydrogenase (LDH), ALT/AST, AST/ALT, creatinine, urea nitrogen (BUN), glucose and electrolytes, cholesterol and HDL-C and LDL-C, triglycerides, LH, FSH, prolactin, TSH, T3, T4. Urinalysis was performed: Sediment, culture, colony counts and antibiotic, if necessary. A pregnancy test was performed (serum or urine, females only). ECG and EEG were performed.

Results

Pharmacokinetics

For Cohort A, pharmacokinetic samples were obtained at baseline and at 0.5, 1.0, 2.0, 6.0, 12.0, 24, 36 hours, and 7 days post dose. For Cohort B, the collection times were modified to account for the elimination phase rate constant and the half-life to the following times: baseline and 0.25, 0.5, 1.0, 2.0, 6.0, 9.5, 10.25, 11, 12, 16, 22, 35 72, 96 and 168 hours, and 7 days post initial dose (a second dose was administered 10 hours after the initial dose). Results are summarized in TABLE 15 for cohort A and TABLE 16 for cohort B.

TABLE 15

Summary pharmacokinetic parameters of 18-MC, M2, M4 and M5 based on individual subjects' parameters, cohort A (20 mg PO single dose)

| Analyte | | Half-Life (hr) | Tmax (hr) | Cmax (ng/mL) | AUCall (hr*ng/mL) | AUCinf (hg*ng/mL) |
|---|---|---|---|---|---|---|
| 18-MC | Average | 17.9 | 0.5 | 119 | 339 | 397 |
| | Min | 14.2 | 0.5 | 92 | 241 | 261 |
| | Max | 21.7 | 0.5 | 182 | 447 | 531 |
| M2 | Average | 14.4 | 1.4 | 41 | 563 | 678 |
| | Min | 11.1 | 0.5 | 27 | 504 | 627 |
| | Max | 19.0 | 2.0 | 62 | 684 | 765 |
| M4 | Average | 7.9 | 1.4 | 347 | 2692 | 2799 |
| | Min | 6.3 | 0.5 | 242 | 1897 | 1978 |
| | Max | 9.3 | 2.0 | 528 | 3925 | 4058 |
| M5 | Average | 29.6 | 0.8 | 25 | 210 | 395 |
| | Min | 16.2 | 0.5 | 12 | 105 | 195 |
| | Max | 43.4 | 1.0 | 38 | 359 | 735 |

TABLE 16

Summary pharmacokinetic parameters of 18-MC, M2, M4 and M5 based on the individual subjects' parameters, cohort B (4 mg PO at 0 and +10 hours)

| Analyte | | Half-Life (hr) | Tmax (hr) | Cmax (ng/mL) | AUCall (hr*ng/mL) | AUCinf (hg*ng/mL) |
|---|---|---|---|---|---|---|
| 18-MC | Average | 16.9 | 2.55 | 30 | 195 | 199 |
| | Min | 3.0 | 0.5 | 20 | 124 | 117 |
| | Max | 52.2 | 10.25 | 46 | 400 | 430 |
| M2 | Average | 44.1 | 11.8 | 11 | 391 | 420 |
| | Min | 18.7 | 11 | 8 | 287 | 283 |
| | Max | 97.8 | 12 | 12 | 500 | 570 |
| M4 | Average | 22.1 | 7.3 | 72.3 | 1648 | 1654 |
| | Min | 13.2 | 0.5 | 65 | 1304 | 1296 |
| | Max | 34.3 | 12 | 82 | 1941 | 1975 |
| M5 | Average | 46.8 | 2.9 | 6 | 163 | 185 |
| | Min | 19.8 | 0.5 | 3 | 104 | 145 |
| | Max | 74.7 | 11 | 9 | 208 | 233 |

Samples underwent two analyses: A research assay (LC/MS/TOF) developed by MicroConstants, Inc was used to collect the raw data. The first analysis was to quantitate 18-MC and the known metabolites M2, M4 and M5 (using standard curves included in the run). The second analysis compared the peak heights of 18-MC and all the metabolites that could be identified in terms of relative peak height (M1 through M10, and P1-P3). As the core structure of all of the metabolites is similar, it is very likely that the absorption and ionization is similar to those of the parent. Structures are shown for the metabolites in FIGS. 21A-21J.

After the administration of 18-MC in either cohort A or B the plasma concentrations of 18-MC, M2, M4 and M5 appeared quickly. The $T_{max}$ for 18-MC, M4 and M5 occurred generally within ½ hour and the $T_{max}$ was possibly slightly delayed for M2. After the administration of 20 mg in cohort A, the $C_{max}$ of 18-MC was 119 ng/mL while M4 $C_{max}$ mean concentration is about 2.5 fold higher (347 ng/mL), and the $C_{max}$ of M2 and M5 was slightly lower than the $C_{max}$ of 18-MC. After the 8 mg dose administered as 4 mg at 0 and +10 hours in cohort B, the $C_{max}$ of 18-MC was about 30 ng/mL, and the $C_{max}$ of M4 was 72 ng/mL. The exposure ($AUC_{all}$) after the 20 mg dose of 18-MC was 339 hrs.*ng/L while the exposure of M4 was 2692 hr*ng/mL. The exposures of M2 and M5 were slightly lower than 18-MC. After the second administration of the 4 mg dose (total of 8 mg) the exposure of 18-MC ($AUC_{all}$) was 195 hr*ng/mL while that of M4 was 1648 hr*ng/mL. The pharmacokinetics appeared to follow a multiple-compartment model (see FIG. 17). After the 20 mg dose, the sampling interval was short compared to the elimination half-life, so the data should be considered preliminary. After the 4 mg at 0 and +10 hours (8 mg total), with the longer sampling interval the elimination half-life of 18-MC and the metabolites was about 48 hours. Comparing the 8 mg dose of 4 mg given twice to the single 20 mg dose, the $C_{max}$ after the 20 mg dose increased proportionally compared to the initial 4 mg dose while the exposure (AUC) increased slightly less then proportionally (2-fold versus an increase in dose of 2.5-fold).

The relative concentrations of the metabolites were determined using peak-heights, with 16 different metabolites identified. Based on exposure of total drug-related substance (calculated as the sum of the AUCs from all of the metabolites plus 18-MC), 18-MC was only a very minor amount of the circulating drug-related material (ranging from 4 to 9 percent). After the 20 mg single dose, M4 was the only major metabolite while M8 was borderline (percentage of the exposure between 8 and 10%). After the administration of 4 mg twice at 0 and +10 hours (total 8 mg), the relative major metabolites changed. Only two metabolites were present at greater than 10% of the total drug related material; M4 (about 40%) and P10, while the exposure of M8 was less than 10% of the total drug related material. P10 accumulated very late ($T_{max}$ ranging from 6 to 10 hours) with a very long elimination half-life that did not allow for appropriate estimation (probably many days) of the elimination rate constant and half-life. As P10 appears as a major metabolite and the elimination could not be adequately determined, the total drug related exposure (to infinity) was not adequately characterized.

Safety

Safety was monitored by reported adverse events, hematology, serum chemistries (including electrolytes, renal and liver function, urinalysis, ECG and vital signs. In addition, a neurological examination (mini-mental status exam) including assessment for abnormal eye movement, nystagmus, tremors, reflexes, upper and lower extremity strength, distal sensor perception, intention tremor, the Romberg test, excessive somnolence and mental status were performed.

Adverse Events

No serious adverse events occurred. The following TABLE 17 summarizes the reported adverse events:

TABLE 17

| | AE Description | Day Noted | Severity | Study Drug related[1] |
|---|---|---|---|---|
| Active Subject | | | | |
| A1 | Nausea | 1 | 1 | 2 |
| A1 | Arterial Hypotension | 1 | 1 | 2 |
| A1 | Pain - submandibular lymph node | 1 | 1 | 2 |
| A1 | Urinary tract infection | 2-30 | 2 | 1 |
| A2 | Retro-orbital headache - right after medication, during about 15 minutes (patient said it after hearing the other patient report the same event.) | 1 | 1 | 2 |
| A3 | Hot coffee burn in hand and right forearm | 7 | 1 | 1 |
| A4 | Dry cough (±1 minute after 18MC administration/ lasted about 10 minutes) in the two administrations* | 4 | 1 | 3 |
| A5 | Body pain | 30 | 1 | 1 |
| A6 | Occipital and frontal headache (lasted ±3 hours) | 4 | 2 | 1 |
| Placebo Subject | | | | |
| P1 | Retro-orbital headache - right after medication, during about 15 minutes (patient said it after hearing the other patient report the same event.) | 1 | 1 | 2 |
| P1 | Sore throat | 1 | 1 | 1 |
| P2 | Dry cough (at 07:00 h, lasting ±05 minutes) | 3 | 1 | 1 |
| P2 | Flu | 4 | 1 | 1 |
| P3 | Occipital headache (started at: ±20:30 h/lasted: 2 hours) | 2 | 2 | 2 |
| P3 | Sensation of "shock" in the left hand when moved, right above of the index finger, where the venous catheter was used | 7 | 1 | 1 |
| P3 | Bloated feeling | 30 | 1 | 1 |
| P3 | Sensation of shock and pain in the left hand | 30 | 1 | 1 |

*CRF entry error. No drug was dosed on day 4.
[2] STUDY DRUG RELATED
1 Not related, 2 Possible, 3 Probable.

Clinical Observations

No clinically significant laboratory abnormalities were noted in any volunteer. The Principal Investigator evaluated each result outside of the laboratories normal range and determined they were 'not clinically significant (NCS)'.

No clinically significant abnormalities on electrocardiograms (ECGs) were noted on the Case Report Forms by the clinical investigators. One Subject in cohort A presented with a disturbance in right bundle branch conduction on Day 30 that was determined not to be of clinical significance.

No clinically significant abnormalities on electroencephalographs (EEGs) were noted on the Case Report Forms.

No clinically significant abnormalities occurred on neurological examination were noted on the Case Report Forms.

Case Reports

Subject 004A1 is a 26 year old healthy small female who entered the study on 7/3/14 in cohort A for screening. Her weight is 45.8 Kg and height 159 cm with a BMI of 18.2. Vital signs on screening were normal (BP 110/70, Temp 37.2, RR 20, and HR 103), although HR was a little high at 103. Physical exam and screening laboratories were normal although Hb was borderline normal at 12.9. ECG and mental status examination were unremarkable. The subject began study treatment on 7/9/14 and vital signs prior to dosing were normal as was the HR at 76 (BP 120/80, RR 20, temp 36.8, HR 76). Her Hb at this time was slightly abnormal at 12.4 (but not deemed clinically significant in a young healthy female). At 08:28 the subject received a single dose of 20 mg 18-MC as per protocol. By 08:58 (30 minutes post dosing), the subject was experiencing nausea and her blood pressure measured 80/60. The subject was treated symptomatically and within 15 minutes the blood pressure returned to normal and nausea resolved within 30 minutes.

Both AE's were rated as grade 1 and possibly related. Blood tests at this time (30 minutes post dosing) showed normal chemistry (Na 141.3, K 4.2 and CI 107) and Hb slightly below normal range at 12.2. Blood was drawn 30 minutes later (1 hour post dosing) and showed normal Na (145) and K (3.6) with an abnormal CI (114) and Hb 11.6. Next blood draw at 2 hours post dosing showed normal K and slightly elevated Na (147.5) and CI (115) and Hb (11.9). At 6 hours post dosing, subject's laboratories showed a borderline high Na (145), and CI (121) and a lower than normal Ca (7.2) and total protein (5.25) with a Hb 12.0. At 12 hours her electrolytes were normal except for a slightly elevated CI (113) and an elevated glucose (114) with a Hb 11.9. By 24 hours, the subject's blood chemistries were normal except for a slightly elevated CI (111). Hb was normal at 12.7. However, the subject had 8 leukocytes in her urine. The subject was monitored in the Clinical Unit for another 12 hours, and prior to discharge all chemistries and hematology were normal except for urinalysis which had >50 leukocytes. This was classified as a grade 2 AE (urinary tract infection) of possible relationship. All other examinations (VS, ECG, mental status exam) during the 36 hours were unremarkable. This subject (as were the other subjects in the cohort) were followed for 30 days post treatment and there were no further adverse events.

Plasma 18-MC levels and metabolites were measured, and although the subject was at the lower limits of BMI (18.2), PK analysis demonstrated that 18-MC and its major metabolite M4 were in the mean average range for the group of 4 subjects treated in Cohort A (20 mg 18-MC single dose). However, it should be noted that the 20 mg single dose generated plasma 18-MC levels that were much higher than expected based on pre-clinical toxicology studies.

In summary, Subject 004A1 received a 20 mg single dose of 18-MC and experienced a hypotensive event with nausea about 30 minutes post dosing. The subject was treated symptomatically and recovered within 15-30 minutes. Post event there were some electrolyte abnormalities most notably Cl and a slight decrease in Hb to below normal levels which lasted about 12 hours. At 24 hours the chemistry and hematology tests were normal but the subject was noted to have leukocytes in her urine and by 36 hours post dosing the subject was diagnosed with a UTI. These adverse events were possibly related although it cannot be ruled out that all findings could be accounted for by anxiety (note: screening HR=103) in a small female with a borderline low HB and a smoldering UTI.

Conclusion

This was a first in human study for 18-MC. The starting dose of 20 mg was selected based on regulatory criteria of starting with 1/10 the NOAEL in the most sensitive species; in this case the mouse. Due to unexpected higher plasma levels in the 20 mg single dose cohort, the dose for the second cohort was lowered to 8 mg (4 mg b.i.d.). 18-MC was tolerated in a dose range of 8 mg to 20 mg. TEAE's that may be study article related were grade 1 and mild in nature for either hypotension or headache. Because 18-MC has a short distribution half-life and longer terminal half-life, the second cohort, cohort 2 was dosed twice a day (b.i.d) for a single day. The b.i.d. dose was chosen so that the subjects would have significant exposures throughout the first day The PK over the dose range from 4 mg to 20 mg was relatively linear for both $C_{max}$ and AUC. Because of the safety assessment and the observation that the PK analysis demonstrated relatively linear PK over the dose of range of 4 mg to 20 mg, it was determined that there was no further scientific/medical need to continue the study for a third cohort dose of 16 mg (8 mg b.i.d.) as would be allowed in amendment #2.

18-MC was safe when administered in doses up to 20 mg in the healthy volunteers in this FIH study and is appropriate for advancement to a multi-ascending dose clinical trial.

Example 7

Study Objective

The objective of this study was to determine the functional activities of the M4 and M5 metabolites of 18-MC HCl at the rat α3β4 nicotinic acetylcholine receptor (nAChR) and to compare their potencies to the parent compound. Studies were performed in HEK 293 cells expressing rat recombinant receptors, voltage clamped at −70 mV and tested by fast perfusion.

Patch-Clamp Recording

Human embryonic kidney 293 fibroblasts (ATCC CRL1573) were cultured in minimum essential medium supplemented with 10% fetal bovine serum and 2 mM glutamine (Life Technologies). Cells were transfected using Lipofectamine 2000 (Life Technologies) with cDNA's for the rat nicotinic αβ and β4 receptor subunits at a 1:1 ratio with enhanced green fluorescent protein (10% of total cDNA, w:w) included as a visual marker for transfected cells. Functional analyses were performed between 16-42 hours post-transfection. Cells were examined by voltage-clamp recording at −70 mV in the whole-cell configuration using an Axopatch 200A patch-clamp amplifier (Axon Instruments). Thin-walled borosilicate glass microelectrodes (TW150F, World Precision Instruments) had resistances of 3-5 MΩ when filled with an internal solution containing (in mM): 135 CsCl, 10 CsF, 10 HEPES, 5 EGTA, 1 MgCl2, and 0.5 CaCl2) at pH 7.2. Current responses were filtered at 5 kHz with an 8-pole Bessel filter (Cygnus Technologies), digitized at 1 kHz, and stored on a Macintosh PowerPC-G3 computer using an ITC-16 interface (Instrutech) under control of the data acquisition and analysis program Synapse (Synergy Research). Cells were continuously superfused with extracellular solution containing (in mM): 150 NaCl, 3 KCl, 5 HEPES, 1 MgCl2, 1.8 $CaCl_2$), 10 glucose, and 0.1 mg/ml phenol red, pH 7.3. Control, agonist, and test article solutions were applied to individual cells by rapid perfusion with a 30 s inter-trial interval. Solutions were driven by a syringe pump through a flowpipe having 6 or 8 inputs that converge at a single common output of approximately 100 μm diameter. Rapid switching between inputs was achieved using a set of upstream solenoid valves (Lee Co.) under computer control.

IC50 Determination

Metabolites (M4 and M5) at concentrations from 1 to 30 μM were tested for inhibition of 1 mM ACh-evoked currents in recombinant α3β4 receptors using methods previously described (Pace et al., 2004). These experiments used an 8-barrel flow pipe to deliver ACh alone or ACh plus varying concentrations of the test metabolite in the same cells in ascending order. The solution exchange protocol delivered a 5 second ACh pulse (1 mM) having 2 second combined application of M4 or M5 delivered in the middle of the ACh pulse. Recordings of 7-8 cells were collected per concentration. ACh-evoked current amplitudes were compared across conditions, and 1050 values were determined by fitting the dose-inhibition curves to the current amplitude measures relative to ACh controls; curve fits are given for the logistic equation: I=Imax/(1+[drug]/IC50). Metabolite association and dissociation kinetics were determined by single-exponential fits to the current decays related to the onset of block and recovery from block, respectively, of 1 mM ACh-evoked currents by 30 μM metabolite.

Kinetic profiles: The kinetics of block and recovery were recorded at a fixed concentration of 30 μM M4 (10×IC50) or M5 metabolite (~IC35) from data obtained by the 1050 protocol described above. Three complementary assays were performed to test M4 or M5 actions on 1 mM ACh-evoked currents in recombinant α3β4 receptors: (1) Simultaneous combined application of M4 or M5 with ACh was used to measure the extent of block and the rates of onset of block from the resting state. (2) Combined M4 or M5 with ACh application following pre-exposure to M4 or M5 was used to measure the extent of block and the rates of onset of block from the drug-bound state. (3) ACh application alone following pre-exposure and removal of M4 or M5 was used to measure the intrinsic ACh current decay rate (desensitization) from the drug-bound state and to confirm that M4 or M5 binding can occur in the absence of ACh activation.

Test Article and Vehicle Formulations

18-MC HCl (lot no. OBI-215-21-3) was obtained from Obiter Research. M4 and M5 were provided by Savant HWP. Solid compounds were stored at −20° C. in a drying desiccator. LC-MS analysis of M4 and M5 are provided in the Appendix. Test articles were dissolved in DMSO to prepare 10 mM stocks of 18-MC HCl and 20 mM stocks of M4 and M5. 1 M acetylcholine stocks were made up in extracellular solution. Stocks were stored frozen at −20° C.

Perfusion solutions containing ACh, 18-MC HCL, M4 or M5 were prepared freshly by dilution to the appropriate concentrations in extracellular solution containing 150 mM NaCl, 3 mM KCl, 5 mM HEPES, 1 mM MgCl2, 1.8 mM CaCl2), 10 mM glucose, and 0.1 mg/ml phenol red adjusted to pH 7.3 with NaOH.

Results

IC50 Determination

Metabolite 1050 values were determined as previously described for 18-MC HCl using a combined application protocol whereby varying metabolite concentrations up to 30 µM were co-applied during 1 mM ACh-evoked currents. Metabolite pulses were 2 sec duration during a 5 sec ACh-evoked response. Example traces are shown in FIGS. 18A, 18C, which illustrate the dose-dependent inhibition of ACh-evoked currents. Using this same protocol, the 1050 for 18-MC HCl was previously resolved at 0.75 µM (Pace et al., 2002), which is re-plotted in FIG. 18E for reference. In the present experiments, IC50 values for the M4 and M5 metabolites were 2.6 µM and 57 µM, respectively. Note, however, because M5 was very weak, the M5 IC50 value was estimated by extrapolation beyond the highest 30 µM concentration tested. Similar results were seen using combined application for 2 sec without ACh pre-exposure (FIGS. 18B, 18D).

Kinetic Parameters

Using current traces derived from the highest concentrations tested, we estimated several kinetic parameters related to metabolite inhibition. The metabolite results are shown in FIGS. 18A-18E and summarized in TABLE 18. The drug association and dissociation rates were derived as follows: $k_{on}$ is given as the reciprocal of the exponential time constant fitting the rate of inhibition (τblock); $k_{off}$ is given as the reciprocal of the exponential time constant fitting the rate of recovery from block (τrecov). Persistent inhibition at 1 second after removal of drug is an index of the stability of the bound state when $k_{off}$ is too slow to be reliably measured. Of note, both M4 and especially M5 appear to dissociate much faster than 18-MC HCl from the α3β4 receptors, while M5 also exhibits a considerably slower association rate suggesting that this metabolite introduces an electrostatic or steric incompatibility with binding to the modulator binding site.

TABLE 18

Kinetic Parameters of 18-MC and Metabolites M4, M5

| Test Compound | kon (s−1) | koff (s−1) | Max Inhibition 20-30 µM (%) | Persistent Inhibition at 1 sec (%) |
|---|---|---|---|---|
| 18-MC HCl | 5.5 ± 0.4 | nd | 98 ± 1 | 88 ± 3 |
| M4 | 4.5 ± 0.4 | 2.5 ± 0.4 | 88 ± 3 | 21 ± 3 |
| M5 | 2.2 ± 0.4 | 6.2 ± 0.2 | 36 ± 5* | 2 ± 2* |

M4 and M5=30 µM; 18-MC HCl=20 µM (from Kuehne et al., 2003); nd=not determined because the rate of recovery was too slow to fit. *Maximum inhibition and persistent inhibition at 1 sec for M5 were measured at 30 µM which was a non-saturating concentration less than 10× of its IC50.

Activity Profiles

In previous experiments, it was noted that 18-MC HCl could pre-bind nAChRs in the absence of ACh and continued to accelerate the ACh-evoked current decay even after removal of drug. Such a profile indicates that the faster decay of ACh-evoked current is due to intrinsic changes in nAChR kinetics when 18-MC HCl is bound, not to onset of block induced by 18-MC binding (see FIG. 19A-19B).

30 µM concentrations of M4 and M5 metabolites were tested in similar manner to determine if they had similar activity. With respect to M4, the 30 µM concentration is approximately 10-times its IC50, comparable to the 10 µM 18-MC HCl shown. With respect to M5, the 30 µM concentration is less than its IC50. As illustrated in FIGS. 20A-20D and summarized in TABLE 19, the M4 metabolite caused rapid block of ACh-evoked currents when co-applied, like 18-MC. Peak ACh-evoked currents were reduced by 68±2% when M4 was co-applied and by 86±2% when M4 was pre-applied and persisted during the ACh pulse. Unlike 18-MC, however, the M4 metabolite did not accelerate the ACh-evoked current decay after pre-exposure and removal. Rather, M4 pre-exposure abolished the peak of the ACh-evoked current and slowed its onset to the normal steady-state level. It is unclear from these experiments alone whether such behavior implies a mechanism of action that differs from that of 18-MC HCl. Rather, it can be explained entirely by the faster dissociation of M4 and lack of persistent inhibition. In either case, the results demonstrate that M4 can pre-bind to inhibit nAChRs in the absence or presence of agonist. Not surprisingly, given that M5 is comparably weak and dissociates rather quickly, no effect was seen after pre-incubation and removal of the M5 metabolite.

TABLE 19

18-MC and Metabolite Activity Profiles

| | Ipeak (% of ACh) | Iss (% of peak) | τdecay (msec) |
|---|---|---|---|
| Control → ACh | 100 | 63 ± 4% | 568 ± 24 |
| Control → ACh + M4 | 23 ± 2% | 24 ± 4% | 236 ± 25 |
| M4 → ACh + M4 | 14 ± 2% | 40 ± 6% | 205 ± 40 |
| M4 → ACh | 42 ± 3% | 97 ± 3% | † |
| M5 → ACh | 70 ± 4% | 62 ± 4% | 554 ± 32 |
| 18MC → ACh | 50 ± 4% | 34 ± 5% | 298 ± 23 |

Concentrations as follows: ACh (1 mM), M4 (30 µM), M5 (30 µM), 18MC (10 µM).
† Current was slow onset and non-desensitizing (τon 131 ± 17 msec).

The M4 metabolite pre-binds in the absence of ACh and blocks more completely when pre-applied. However M4 dissociates more quickly than 18-MC HCl such that solution jumps from M4 to ACh alone caused a slow onset response with no peak. The lower affinity M5 metabolite dissociates even faster, such that jumps from M5 to ACh alone had no effect on ACh-evoked currents. (Shown: 1 mM ACh; 30 µM M4, M5).

Additional information on the metabolites is shown in TABLE 20.

TABLE 20

| Name | Found m/z | Original $T_R$, min | New $T_R$, min | Assigned Identity | Molecular Formula | Theoretical m/z | Mass Difference[a] | | From Parent |
|---|---|---|---|---|---|---|---|---|---|
| | | | | | | | mDa | PPM | |
| Parent | 369.2164 | 8.82 | 8.6 | 18-Methoxycoronaridine | C22H28N2O3 | 369.2178 | −1.4 | −3.8 | −0.0014 |
| M2 | 353.1858 | 5.46 | 5.23 | Demethylation + Desaturation | C21H24N2O3 | 353.1865 | −0.7 | −2.0 | −16.0320 |

TABLE 20-continued

| Name | Found m/z | Original $T_R$, min | New $T_R$, min | Assigned Identity | Molecular Formula | Theoretical m/z | Mass Difference[a] | | From Parent |
|---|---|---|---|---|---|---|---|---|---|
| | | | | | | | mDa | PPM | |
| M3 | 355.2014 | 6.80 | 6.42 | Demethylation | C21H26N2O3 | 355.2021 | −0.7 | −2.0 | −14.0164 |
| M4 | 367.2027 | 8.60 | 8.40 | Desaturation | C22H26N2O3 | 367.2021 | 0.6 | 1.6 | −2.0151 |
| M5 | 369.1816 | 7.52 | 7.31 | 2-Ethoxyl to Acid | C21H24N2O4 | 369.1814 | 0.2 | 0.5 | −0.0362 |
| M8 | 383.1970 | 5.53 | 5.13 | Hydroxylation + Desaturation | C22H26N2O4 | 383.1971 | −0.1 | −0.3 | 13.9792 |
| M9 | 383.1956 | 6.21 | 5.83 | Hydroxylation + Desaturation | C22H26N2O4 | 383.1971 | −1.5 | −3.9 | 13.9778 |
| M12 | 531.2336 | 5.00 | 4.54 | Demethylation + Glucuronide Conjugation | C27H34N2O9 | 531.2342 | −0.6 | −1.1 | 162.0158 |
| P2 | 373.2114 | 6.59 | 6.20 | Demethylation + Hydroxylation + Reduction | C21H28N2O4 | 373.2127 | −1.3 | −3.5 | 3.9936 |
| P5 | 383.1982 | — | 10.73 | Hydroxylation + Desaturation | C22H26N2O4 | 383.1971 | 1.1 | 2.9 | 13.9804 |
| P7 | 387.2295 | 8.91 | 8.52 | Hydroxylation + Reduction | C22H30N2O4 | 387.2284 | 1.1 | 2.8 | 18.0117 |
| P10 | 529.2192 | 3.33 | 3.13 | Desaturation + Demethylation + Glucuronide Conjugation | C27H32N2O9 | 529.2186 | 0.6 | 1.1 | 160.0014 |

[a]Mass Difference represents the difference between m/z Found and Theoretical m/z in both milliDalton (mDa) and parts per million (PPM). The difference of the Found m/z from the Theoretical m/z for the parent molecule is also reported.

Chemical names for several of the metabolites are as follows:

M2: methyl7-(2-hydroxyethyl)-7,8,9,10-tetrahydro-5H-6,9-methanopyrido[1',2'1,2]azepino[4,5-b]indole-6(6aH)-carboxylate M3: methyl7-(2-hydroxyethyl)-7,8,9,10,12,13-hexahydro-5H-6,9-methanopyrido[1',2'1,2]azepino[4,5-b]indole-6(6aH)-carboxylate M4: methyl7-(2-methoxyethyl)-7,8,9,10-tetrahydro-5H-6,9-methanopyrido[1',2'1,2]azepino[4,5-b]indole-6(6aH)-carboxylate M5: 2-(6-(methoxycarbonyl)-6,6a,7,8,9,10,12,13-octahydro-5H-6,9-methanopyrido[1',2'1,2]azepino[4,5-b]indol-7-yl)acetic acid M8: methyl 2-hydroxy-7-(2-methoxyethyl)-7,8,9,10-tetrahydro-5H-6,9-methanopyrido[1',2'1,2]azepino[4,5-b]indole-6(6aH)-carboxylate M12: (2S,3S,4S,5R,6R)-3,4,5-trihydroxy-6-(2-(6-(methoxycarbonyl)-6,6a,7,8,9,10,12,13-octahydro-5H-6,9-methanopyrido[1',2':1,2]azepino[4,5-b]indol-7-yl)ethoxy)tetrahydro-2H-pyran-2-carboxylic acid P10: (2S,3S,4S,5R,6R)-3,4,5-trihydroxy-6-(2-(6-(methoxycarbonyl)-6,6a,7,8,9,10-hexahydro-5H-6,9-methanopyrido[1',2'1,2]azepino[4,5-b]indol-7-yl)ethoxy)tetrahydro-2H-pyran-2-carboxylic acid Conclusions Two major metabolites of 18-MC HCl, M4 and M5 (shown in FIGS. 21A and 21B), were tested in HEK 293 cells co-transfected with rat αβ and β4 subunit cDNAs. Both metabolites inhibited ACh-evoked currents with IC50 values of 2.6 µM for M4 and 57 µM for M5. These values are approximately 3.5- and 76-fold less potent, respectively, than the parent 18-MC HCl. The kinetics rates for M4 at 30 µM were kon 4.5 sec-1, koff=2.5 sec-1 and the persistent inhibition at 1 sec after removal was 21±3%. The kinetic rates for M5 at 30 µM were kon 2.2 sec-1, koff=6.2 sec-1 and the persistent inhibition at 1 sec after removal was 2±2%.

The activity profiles are generally consistent with M4 and M5 retaining some activity of 18-MC HCl, albeit with much reduced potency. The only phenotypic difference noted was the slow onset to steady-state of ACh-evoked currents following removal of M4 compared to 18-MC HCl, but this difference is entirely consistent with its faster dissociation from the receptor.

Example 8

The purpose of the present study was to evaluate the effects of 18-MC HCl on lever pressing rates in rats maintained by intracranial self-stimulation (ICSS) using a frequency-rate procedure. Doses of 18-MC HCl (10, 40, 56 mg/kg) and vehicle (0.01 M NaH2PO4 in sterile water) were tested. Compared to vehicle, 18-MC HCl did not affect frequency-rate curves of ICSS, the estimated frequency that supports half-maximal responding (M50), nor threshold responding (T0). Behavioral effects (loss of righting reflex, ataxia, ptosis) were observed in rats treated with all doses of 18-MC HCl approximately 5 minutes after injection, but rats appeared to have recovered prior to the start of the operant session (45 minutes after 18-MC HCl administration). Overall, these data suggest that 18-MC HCl does not alter responding reinforced by medial forebrain bundle stimulation under these conditions.

Background

ICSS involving electrical stimulation of the medial forebrain bundle is thought to result in activation of myelinated neurons that engage dopaminergic dendrites or cell bodies of the VTA and substantia nigra that subsequently send efferent, ascending projections throughout the mesocorticolimbic system. Drugs of abuse, such as nicotine, amphetamine, and the opiates generally enhance ICSS by reducing the threshold frequency or intensity that supports this behavior and this effect is hypothesized to correlate with their abuse-related effects. Conversely, drugs that produce anhedonia or dysphoria, such as the neuroleptics, lithium, or K-opioid agonists, generally increase the threshold frequency or intensity that supports this behavior.

The present study evaluated 18-MC HCl for its ability to alter ICSS. Accordingly, rats were tested with vehicle, then 18-MC HCl (10, 40, and 56 mg/kg) given in a semi-randomized order, and once again tested with vehicle to assess stability over time.

Methods

Subjects

Eleven adult experimentally naïve male Sprague-Dawley rats (Harlan, Indianapolis, Ind.) were individually housed in a temperature-controlled (20-22° C.) AAALAC-accredited facility in which they had restricted access to food (7012 Teklad LM-485 Mouse/Rat Sterilizable Diet; Harlan, Indianapolis, Ind.) for maintaining a weight range of 380-420 g, and ad libitum access to water. The rats were maintained on a 12 hour/12 hour light-dark cycle (0600-1800 lights on) for the duration of the experiment, and they were trained and tested during the light segment of this cycle. Rats (360-420 g at time of surgery) were anesthetized via isoflurane inhalation (~3%) and an electrode was implanted into the medial forebrain bundle according to stereotaxic coordinates, anteroposterior: −2.8 mm from bregma, lateral: 1.7 mm from the midline, ventrodorsal: −7.8 mm from skull (Paxinos & Watson, 2007).

Apparatus

Experimental sessions were conducted in standard operant conditioning chambers enclosed in sound-attenuating cubicles each with a ventilation fan and featured two retractable levers on the front intelligence panel, a stimulus lamp above each lever, and a 5-W house light (Med Associates, St. Albans, Vt.). A counterbalanced tether (Plastics One, Roanoke, Va.) connected the electrode to an ICSS stimulator (product number PHM-152/2, Med Associates, St. Albans, Vt.), allowing free movement within the operant chamber.

Procedure

One week after surgery, the rats began fixed ratio 1 (FR1) self-stimulation training. Initially, both left and right levers were extended, the house light illuminated, and each press of the right-side lever (i.e., FR1) resulted in the delivery of stimulation (100 pA, 158 Hz). Responses on the left lever were without programmed consequences. During the duration of the delivery of stimulation (500 ms), the house light was extinguished and the cue lights above each lever flashed at 3 Hz. Current intensity was individually adjusted when necessary to maintain stable maximal rates of behavior (>40 responses/min) at the highest frequency. This intensity level was held constant for the remainder of the experiment.

The frequency-rate procedure (modified from Carlezon & Wise, 1996) consisted of multiple (see below) components, each composed of 10, 1-minute FR 1 reinforcement periods. During each 1-minute reinforcement period, a single, scheduled frequency was available for delivery contingent upon FR 1 responding. Frequencies were progressively decreased in 0.05 log-increments from 158-56 Hz (i.e. 2.2-1.75 log Hz) during each component. Each 1-minute reinforcement period was preceded by a 5-second sample period during which five non-contingent stimulations were delivered at the scheduled stimulation frequency. Each response period was followed by a 5-second timeout (T0) period during which the house light was extinguished and ICSS was unavailable. Rats were trained daily (M-F) using the described procedure. Training sessions were conducted in the morning and consisted of three consecutive components. Once stable behavior was established, as demonstrated by <10% variation in threshold (i.e. theta 0; T0) and M50 (see Data Analysis) for three consecutive sessions, animals began testing, and baseline stability was monitored throughout the course of the experiment. Threshold (T0) is the theoretical frequency at which the linear portion of the frequency-rate curve intersects with the abscissa (i.e., zero responses). M50 is the estimated frequency that supports half-maximal responding.

On test days, two ICSS experimental sessions were conducted. During the baseline session, each rat was tested during three consecutive components identical to training days. After completing this baseline determination, rats were returned to their home cages and then received an i.p. injection of either 18-MC HCl (10, 40, or 56 mg/kg) or vehicle [0.01M NaH2PO4, Sigma Cat # S0751, Sigma Aldrich, St. Louis, Mo.] 45 minutes prior to the test session. Rats were returned to operant chambers for the test session that consisted of two consecutive components (i.e., two complete frequency sweeps). Doses of 18-MC HCl were determined according to a semi-randomized order.

Subjects were tested up to twice weekly (typically Tuesday and Friday), with a minimum of 72 hours between test sessions. Frequency-rate training sessions were conducted during the week on non-test days to maintain and monitor stability in frequency-rate responding, and to determine testing eligibility. Rats were required to meet stability criteria (<10% variation in threshold and in the M50 from the last baseline test session) in order to be scheduled for testing. One to two frequency-rate training sessions were conducted between test sessions to assess behavioral stability.

Data Analysis

Two rats were excluded from data analyses. One was excluded because of unstable baseline performance, and one was removed due to electrode patency, thus, the results included in this report are from nine rats. Results from the initial component during baseline sessions on test days were excluded from the data analysis as it has been shown that behavior is less stable during the first daily experimental component relative to subsequent components. Results obtained at each frequency during each of the two subsequent baseline components were averaged to determine a baseline response rate for each frequency. Maximum control response rate (MCR) was then defined by the maximum baseline response rate that occurred across all frequencies during the baseline session. For subsequent data analyses, individual rat results during the baseline and test sessions were then normalized to a rat's MCR to produce percent maximum control rate (% MCR) scores by dividing the mean number of responses obtained at each frequency by the rat's MCR as determined during the associated (i.e., the same day's) baseline session, and then finally multiplying this quotient by 100, separately for the baseline and test sessions.

Frequency-rate response data were analyzed using two-way (treatment×frequency) repeated measures ANOVAs, followed by Holm-Šídák multiple comparisons tests to identify treatment-related differences in responding at each frequency. For all frequency-rate curves, vehicle served as the comparison condition. Parallel leftward shifts in the frequency-rate curve may be indicative of reward facilitation, and parallel rightward shifts in the frequency-rate curve can be indicative of reward attenuation. Upward (rate increasing) or downward (rate decreasing) shifts in the frequency-rate curve at maximum response rates may be indicative of nonspecific motoric effects.

In addition to frequency-rate response curves, additional summary dependent measures were calculated and analyzed. Threshold (T0) is the theoretical frequency at which the linear portion of the frequency-rate curve intersects with the abscissa (i.e., zero responses). M50 is the estimated frequency that supports half-maximal responding (i.e. 50%). Log transformations of frequency-rate curves were calculated using linear regression analysis to determine the T0 and M50 for each animal at each dose tested. T0 and M50 log frequency values were determined for each baseline and corresponding test session and analyzed using one-way repeated measures ANOVA for each condition (baseline and test), and multiple comparisons were made using Fisher's LSD test to compare all 18-MC HCl doses to vehicle control. In addition, T0 and M50 raw frequencies after drug administration were normalized to baseline values (percent baseline T0 and M50), analyzed using repeated measures ANOVA and multiple comparisons were conducted using Fisher's LSD test. All statistical tests were conducted using microcomputer software (Prism 6, GraphPad Software, Inc., San Diego, Calif.), and all types of comparisons were considered statistically significant if p<0.05.

Observational Notes

Visual signs of impairment/intoxication, including loss of righting reflex, ataxia, and ptosis were observed in rats treated with the dose of 18-MC HCl. These effects were prominent approximately 5 minutes following drug administration and were not observed in vehicle-treated rats. After the 45 minutes pretreatment time lapsed, subjects appeared normal in the home cage and upon handling.

Effects of 18-MC HCl on Frequency-Rate ICSS

Frequency-rate results with 18-MC HCl (10-56 mg/kg) and vehicle are presented in FIG. 22. Frequency-rate response curve for the effects of 18-MC HCl (10, 40, 56 mg/kg) or vehicle (0.01 M NaH2PO4). Values represent the mean normalized response rate (% of maximum control responding) across 10 frequency presentations (1.75-2.20 log/Hz) of 9 rats. Error bars are omitted for clarity. There was a significant main effect of frequency [F(9, 72)=106.5, p<0.0001], but no main effect of 18-MC HCl treatment on ICSS [F(3, 24)=0.42, p>0.05], and no interaction [F(27, 216)=0.75, p>0.05]. Specifically, no tested dose of 18-MC HCl (10-56 mg/kg) affected the ICSS frequency-rate curve. Maximal response rates were not altered during 18-MC HCl testing, suggesting that it does not produce generalized motor impairment within the time frame tested.

Figure 23A:
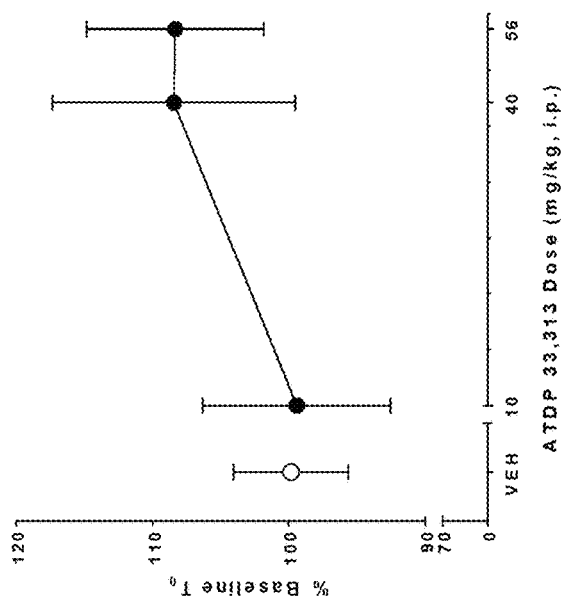
FIG. 23A is a graph of MC-18 effects on T0 and FIG. 23B is a graph of MC-18 effects on M50.
Figure 23B:
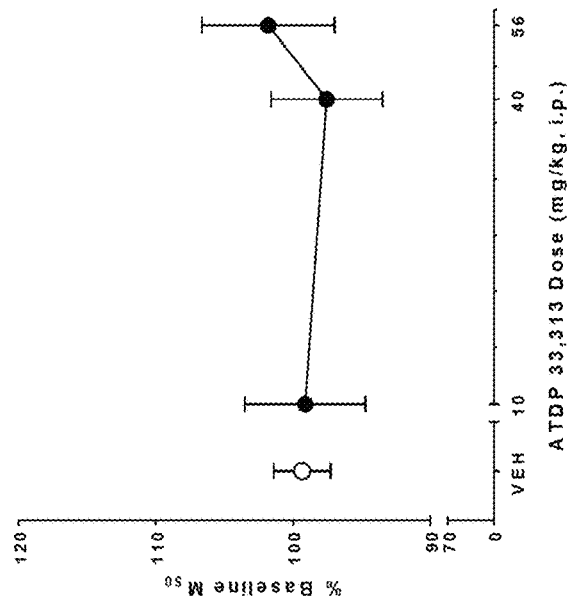

The effects of 18-MC HCl on T0 and M50 levels for all test conditions are presented on FIGS. 23A-23B and TABLES 20-21. Effects of 18-MC HCl on percent baseline T0 and M50 are shown. Values represent means (+SEM) of calculated T0 (top panel) or M50 (bottom panel) normalized to baseline in 9 rats. There were no significant differences compared to vehicle. When normalized to percent baseline, T0 and M50 were analyzed as separate one-way repeated measures ANOVAs (FIGS. 23A-23B). Analysis of T0 data (top panel) revealed there was not a main effect of 18-MC HCl treatment [F(3,24)=0.59, p>0.05]. Similarly, analysis of M50 data (bottom panel) revealed there was not a main effect of drug treatment [F(3,24)=0.24, p>0.05]. Log frequency values for 18-MC HCl and baselines are displayed on TABLES 20 and 21 and did not differ from vehicle values. Importantly, baseline T0's and M50's did not significantly vary during the course of the study (TABLES 20-21). Overall, results from these analyses were consistent with findings from the rate-frequency curve analysis, demonstrating that 18-MC HCl does not alter ICSS under the testing parameters. Given the observation that all doses of 18-MC HCl tested produced a marked alteration in behavior prior to the test sessions, testing may not have occurred within the period of peak behavioral activity. A more thorough characterization of 18-MC HCl, if warranted, would include assessment of 18-MC HCl following shorter pretreatment times.

TABLE 21

| Threshold ($T_0$) | Baseline | Test | N |
|---|---|---|---|
| VEH | 1.81 (0.01) | 1.81 (0.02) | 9 |
| 10 mg/kg 33,313 | 1.81 (0.02) | 1.80 (0.03) | 9 |
| 40 mg/kg 33,313 | 1.83 (0.02) | 1.85 (0.03) | 9 |
| 56 mg/kg 33,313 | 1.82 (0.02) | 1.85 (0.02) | 9 |

TABLE 21 is a summary table of threshold log 10 frequency values (T0) in rats tested with 18-MC HCl (10-56 mg/kg) or vehicle. There were no significant differences in T0 values compared to the VEH condition using Fisher's LSD multiple comparison test. Data represent the mean T0 frequency (log/Hz)+SEM of 9 rats.

TABLE 22

| $M_{50}$ | Baseline | Test | N |
|---|---|---|---|
| VEH | 1.95 (0.01) | 1.94 (0.01) | 9 |
| 10 mg/kg 33,313 | 1.95 (0.01) | 1.94 (0.02) | 9 |
| 40 mg/kg 33,313 | 1.97 (0.02) | 1.95 (0.02) | 9 |
| 56 mg/kg 33,313 | 1.95 (0.01) | 1.95 (0.02) | 9 |

TABLE 22 is a summary table of log 10 frequency values that sustained half-maximal responding (M50) in rats tested with 18-MC HCl (10-56 mg/kg) or vehicle. There were no significant differences in M50 values compared to the VEH condition using Fisher's LSD multiple comparison test. Data represent the mean M50 frequency (log/Hz)+SEM of 9 rats.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of treating substance use disorders, including the steps of:
   administering an effective amount of 18-Methoxycoronaridine salt (18-MC) in a pharmaceutical carrier to an individual, wherein the individual is a human, wherein the 18-MC administered follows a multiple-compartment model and a half-life is about 48 hours; and
   preventing treating substance abuse in the individual, wherein the substance is chosen from the group consisting of cocaine, nicotine, opiates, alcohol, morphine, and methamphetamine.

2. The method of claim 1, wherein said treating preventing step is further defined as reducing reinforcing and rewarding effects of the substance.

3. The method of claim 1, wherein said administering step is performed orally.

4. The method of claim 1, wherein the salt is a hydrochloride salt.

5. The method of claim 1, wherein said administering step is further defined as administering 0.01-10 mg/kg of 18-MC.

6. The method of claim 5, wherein said administering step is further defined as administering 20 mg or less per day of 18-MC.

7. The method of claim 1, further including the step of blocking α3β4 nicotinic receptors in the habenulo-interpeduncular pathway and the basolateral amygdala.

8. The method of claim 1, further including the step of inhibiting enzymes CYP2C9, CYP2C19, CYP2C8, CYP2E1, and CYP3A4.

* * * * *